US011388325B2

(12) United States Patent
Bohling et al.

(10) Patent No.: US 11,388,325 B2
(45) Date of Patent: Jul. 12, 2022

(54) SYSTEMS AND METHODS FOR ASSESSING PRODUCTS

(71) Applicant: Walmart Apollo, LLC, Bentonville, AR (US)

(72) Inventors: Joshua T. Bohling, Centerton, AR (US); Chuck E. Tilmon, Rogers, AR (US); Emily Moneka Francis Xavier, Bentonville, AR (US); Daniel J. Pumford, Rogers, AR (US); Brian J. A. Schardt, Trabuco Canyon, CA (US); Issac Mathew, Karnataka (IN); Venkataraja Nellore, Rogers, AR (US); Gaurav Savlani, Bentonville, AR (US); Viraj C. Patel, Gujarat (IN); Rahul Agarwal, Karnataka (IN); Pushkar Pushp, Karnataka (IN); Jennifer McTeer, Bentonville, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 0 days.

(21) Appl. No.: 16/526,677

(22) Filed: Jul. 30, 2019

(65) Prior Publication Data

US 2020/0275010 A1 Aug. 27, 2020
US 2022/0046164 A9 Feb. 10, 2022

Related U.S. Application Data

(60) Provisional application No. 62/810,129, filed on Feb. 25, 2019.

(30) Foreign Application Priority Data

Nov. 20, 2018 (IN) .............................. 201841043606

(51) Int. Cl.
*H04N 5/232* (2006.01)
*G06V 20/52* (2022.01)
(Continued)

(52) U.S. Cl.
CPC ......... *H04N 5/23203* (2013.01); *G06V 20/46* (2022.01); *G06V 20/52* (2022.01); *G06V 20/64* (2022.01); *H04N 5/2354* (2013.01)

(58) Field of Classification Search
CPC ............ H04N 5/23203; H04N 5/2354; G06K 9/00744; G06K 9/00201; G06K 9/00771
See application file for complete search history.

(56) References Cited

U.S. PATENT DOCUMENTS 4,750,197 A 6/1988 Denekamp
5,369,995 A 12/1994 Scheinbeim
(Continued)

FOREIGN PATENT DOCUMENTS

CA 2469699 1/2016
CN 1789992 6/2006
(Continued)

OTHER PUBLICATIONS

Bevan et al.; "Storage of Organically Produced Crops"; https://orgprints.org/8241/1/Storage_organic_produce_report.pdf; Dec. 1997; pp. 1-227.
(Continued)

*Primary Examiner* — Yogesh K Aggarwal
(74) *Attorney, Agent, or Firm* — Fitch, Even, Tabin & Flannery, LLP

(57) ABSTRACT

In some embodiments, apparatuses, systems, and methods are provided herein useful to assessing products. In some embodiments, an enclosure for use in assessing products comprises a housing including a door configured to allow placement of a product within the housing, a product holding
(Continued)

surface located within the housing allowing pictures to be taken through the product holding surface and configured to support the product, a first image capture device configured to capture an image of the product from a first perspective, a second image capture device configured to capture an image of the product from a second perspective, and wherein the image of the product from the second perspective is captured through the product holding surface, and a lighting element, wherein the lighting element is located within the housing, and wherein the lighting element is configured to provide lighting within the housing.

20 Claims, 3 Drawing Sheets

(51) Int. Cl.
*G06V 20/64* (2022.01)
*G06V 20/40* (2022.01)
*H04N 5/235* (2006.01)

(56) References Cited

U.S. PATENT DOCUMENTS

| | | | |
|---|---|---|---|
| 5,621,162 | A | 4/1997 | Yun |
| 5,671,362 | A | 9/1997 | Cowe |
| 5,774,053 | A | 6/1998 | Porter |
| 5,791,497 | A | 8/1998 | Campbell |
| 5,835,012 | A | 11/1998 | Wilk |
| 6,204,763 | B1 | 3/2001 | Sone |
| 6,285,282 | B1 | 9/2001 | Dorenbosch et al. |
| 6,294,997 | B1 | 9/2001 | Paratore et al. |
| 6,296,187 | B1 | 10/2001 | Shearer |
| 6,386,454 | B2 | 5/2002 | Hecht |
| 6,435,002 | B1 | 8/2002 | Briggs |
| 6,497,367 | B2 | 12/2002 | Conzola |
| 6,549,135 | B2 | 4/2003 | Singh |
| 6,600,418 | B2 | 7/2003 | Francis |
| 6,624,752 | B2 | 9/2003 | Klitsgaard |
| 6,779,722 | B1 | 8/2004 | Mason |
| 6,847,447 | B2 | 1/2005 | Ozanich |
| 6,865,516 | B1 | 3/2005 | Richardson |
| 6,876,990 | B2 | 4/2005 | Yamanishi |
| 6,965,871 | B1 | 11/2005 | Szabo |
| 6,970,100 | B2 | 11/2005 | Lovegreen |
| 6,982,640 | B2 | 1/2006 | Lindsay |
| 7,004,621 | B2 | 2/2006 | Roberts |
| 7,027,958 | B2 | 4/2006 | Singh |
| 7,057,495 | B2 | 6/2006 | Debord |
| 7,065,501 | B1 | 6/2006 | Brown |
| 7,148,803 | B2 | 12/2006 | Bandy |
| 7,185,810 | B2 | 3/2007 | White |
| 7,245,386 | B2 | 7/2007 | Philipps |
| 7,248,147 | B2 | 7/2007 | Debord |
| 7,271,720 | B2 | 9/2007 | Tabe |
| 7,271,724 | B2 | 9/2007 | Goyal |
| 7,287,694 | B2 | 10/2007 | Banavar |
| 7,298,257 | B2 | 11/2007 | Suzuki |
| 7,347,361 | B2 | 3/2008 | Lovett |
| 7,372,003 | B2 | 5/2008 | Kates |
| 7,434,724 | B2 | 10/2008 | Lane |
| 7,450,247 | B2 * | 11/2008 | Sandberg ............ A22C 17/0033 250/223 R |
| 7,455,225 | B1 | 11/2008 | Hadfield |
| 7,487,913 | B2 | 2/2009 | Adema |
| 7,495,558 | B2 | 2/2009 | Pope |
| 7,543,741 | B2 | 6/2009 | Lovett |
| 7,560,013 | B2 | 7/2009 | Shekarriz |
| 7,673,464 | B2 | 3/2010 | Bodin |
| 7,675,424 | B2 | 3/2010 | Debord |
| 7,693,739 | B2 | 4/2010 | Schmidtberg |
| 7,757,947 | B2 | 7/2010 | Reznik |
| 7,769,221 | B1 | 8/2010 | Shakes |
| 7,775,130 | B2 | 8/2010 | Harish |
| 7,792,711 | B2 | 9/2010 | Swafford, Jr. |
| 7,796,038 | B2 | 9/2010 | Batra |
| 7,810,720 | B2 | 10/2010 | Lovett |
| 7,835,885 | B2 | 11/2010 | Ben-Tzur |
| 7,937,244 | B2 | 5/2011 | Kadaba |
| 7,954,712 | B2 | 6/2011 | Babcock |
| 7,960,176 | B2 | 6/2011 | Louvet |
| 7,967,201 | B2 | 6/2011 | Bowlus |
| 7,978,060 | B2 | 7/2011 | Mandava |
| 8,072,605 | B2 | 12/2011 | Costa |
| 8,102,101 | B2 | 1/2012 | Giurgiutiu |
| 8,112,303 | B2 | 2/2012 | Eglen |
| 8,203,603 | B2 | 6/2012 | Harbert |
| 8,279,065 | B2 | 10/2012 | Butler |
| 8,306,871 | B2 | 11/2012 | Farmer |
| 8,325,036 | B1 | 12/2012 | Fuhr |
| 8,334,970 | B2 | 12/2012 | Wildenbeest |
| 8,354,927 | B2 | 1/2013 | Breed |
| 8,412,590 | B2 | 4/2013 | Elliott |
| 8,447,665 | B1 | 5/2013 | Schoenharl |
| 8,626,193 | B1 | 1/2014 | Crossno |
| 8,682,760 | B2 | 3/2014 | Cameo |
| 8,786,407 | B2 | 7/2014 | Liu |
| 8,803,970 | B2 | 8/2014 | Weisensale |
| 8,870,453 | B2 | 10/2014 | Branch |
| 8,947,234 | B2 | 2/2015 | Doan |
| 8,989,053 | B1 | 3/2015 | Skaaksrud |
| 8,994,508 | B2 | 3/2015 | Dacus |
| 9,024,755 | B2 | 5/2015 | Fuhr |
| 9,030,295 | B2 | 5/2015 | Allen |
| 9,031,990 | B2 | 5/2015 | Scott |
| 9,218,585 | B2 | 12/2015 | Gupta |
| 9,244,147 | B1 | 1/2016 | Soundararajan |
| 9,275,361 | B2 | 3/2016 | Meyer |
| 9,316,595 | B2 | 4/2016 | Wakita |
| 9,350,734 | B1 | 5/2016 | Jamshidi |
| 9,366,483 | B2 | 6/2016 | Eckhoff |
| 9,443,217 | B2 | 9/2016 | Iyer |
| 9,449,208 | B2 | 9/2016 | Luk |
| 9,514,323 | B2 | 12/2016 | Mehring |
| 9,524,648 | B1 | 12/2016 | Gopalakrishnan |
| 9,557,224 | B2 | 1/2017 | Eisenstadt |
| 9,569,944 | B2 | 2/2017 | Barnes |
| 9,710,754 | B2 | 7/2017 | Kaye |
| 9,766,114 | B2 | 9/2017 | Ademe |
| 9,789,518 | B2 | 10/2017 | Iino |
| 9,794,165 | B1 | 10/2017 | Wood |
| 9,811,632 | B2 | 11/2017 | Grabiner |
| 9,824,298 | B1 | 11/2017 | Krishnan Gorumkonda |
| 9,835,498 | B2 | 12/2017 | Haarer |
| 9,888,214 | B2 | 2/2018 | Bateman |
| 9,915,638 | B2 | 3/2018 | Pakstaite |
| 10,009,667 | B2 | 6/2018 | Taylor |
| 10,060,798 | B1 | 8/2018 | Riscalla |
| 10,089,556 | B1 | 10/2018 | Xu |
| 10,176,451 | B2 | 1/2019 | Nemet |
| 10,187,593 | B2 | 1/2019 | Holmes |
| 10,223,610 | B1 | 3/2019 | Akselrod-Ballin |
| 10,281,200 | B2 | 5/2019 | Johnston |
| 10,285,433 | B2 | 5/2019 | Ademe |
| 10,324,439 | B2 | 6/2019 | Lagares-Greenblatt |
| 10,373,472 | B2 | 8/2019 | Johnston |
| 10,386,827 | B2 | 8/2019 | Enver |
| 10,423,918 | B2 | 9/2019 | Mehring |
| 10,445,684 | B2 | 10/2019 | Mehring |
| 10,452,959 | B1 | 10/2019 | Gautam |
| 10,466,111 | B2 | 11/2019 | Jones |
| 10,546,162 | B1 | 1/2020 | Diorio |
| 10,552,654 | B2 | 2/2020 | Beckmann |
| 10,572,851 | B2 | 2/2020 | Skaaksrud |
| 10,591,306 | B2 | 3/2020 | High |
| 10,594,956 | B2 | 3/2020 | Holmes |
| 10,676,794 | B2 | 6/2020 | Amini |
| 10,956,856 | B2 | 3/2021 | Ma |
| 11,070,895 | B2 | 7/2021 | Taylor |
| 11,138,554 | B2 | 10/2021 | Johnsen |
| 2001/0045449 | A1 | 11/2001 | Shannon |
| 2002/0119513 | A1 | 8/2002 | Alocilja |

(56) References Cited

U.S. PATENT DOCUMENTS

| | | |
|---|---|---|
| 2003/0088442 A1 | 5/2003 | Michael |
| 2003/0214387 A1 | 11/2003 | Giaccherini |
| 2004/0018641 A1 | 1/2004 | Goldsmith |
| 2004/0069046 A1 | 4/2004 | Sunshine |
| 2004/0074957 A1 | 4/2004 | Devar |
| 2004/0148117 A1 | 7/2004 | Kirshenbaum |
| 2004/0154739 A1 | 8/2004 | Shanahan |
| 2004/0204881 A1 | 10/2004 | Mayer |
| 2004/0226392 A1 | 11/2004 | McNally |
| 2004/0233055 A1 | 11/2004 | Canich |
| 2005/0060246 A1 | 3/2005 | Lastinger |
| 2005/0061877 A1 | 3/2005 | Stevens |
| 2005/0075954 A1 | 4/2005 | Matsumoto |
| 2005/0104730 A1 | 5/2005 | Yang |
| 2005/0149470 A1 | 7/2005 | Fujie |
| 2005/0197912 A1 | 9/2005 | Wittmer |
| 2005/0203790 A1 | 9/2005 | Cohen |
| 2005/0222889 A1 | 10/2005 | Lai |
| 2005/0228712 A1 | 10/2005 | Bornstein |
| 2006/0006987 A1 | 1/2006 | Hashimoto |
| 2006/0011721 A1 | 1/2006 | Olsen, III |
| 2006/0018274 A1 | 1/2006 | Twitchell |
| 2006/0071774 A1 | 4/2006 | Brown |
| 2006/0080819 A1 | 4/2006 | McAllister |
| 2006/0096303 A1 | 5/2006 | Kavounas |
| 2006/0097875 A1 | 5/2006 | Ott |
| 2006/0171332 A1 | 8/2006 | Barnum |
| 2006/0192652 A1 | 8/2006 | Mandava |
| 2006/0238307 A1 | 10/2006 | Bauer |
| 2006/0244718 A1 | 11/2006 | Hiddink |
| 2007/0050070 A1 | 3/2007 | Strain |
| 2007/0050271 A1 | 3/2007 | Ufford |
| 2007/0064765 A1 | 3/2007 | Solie |
| 2007/0067177 A1 | 3/2007 | Martin |
| 2007/0067203 A1 | 3/2007 | Gil |
| 2007/0069867 A1 | 3/2007 | Fleisch |
| 2007/0076779 A1 | 4/2007 | Haarer |
| 2007/0156261 A1 | 7/2007 | Caldwell |
| 2007/0176773 A1 | 8/2007 | Smolander |
| 2007/0221727 A1 | 9/2007 | Reznik |
| 2008/0001752 A1 | 1/2008 | Bruns |
| 2008/0052201 A1 | 2/2008 | Bodin |
| 2008/0067227 A1 | 3/2008 | Poss |
| 2008/0073431 A1 | 3/2008 | Davis |
| 2008/0103944 A1 | 5/2008 | Hagemann |
| 2008/0186175 A1 | 8/2008 | Stern |
| 2008/0292759 A1 | 11/2008 | Palmer |
| 2008/0294488 A1 | 11/2008 | Gupta |
| 2009/0027213 A1 | 1/2009 | Debord |
| 2009/0040063 A1 | 2/2009 | Yearsley |
| 2009/0058644 A1 | 3/2009 | French |
| 2009/0076645 A1 | 3/2009 | Ben-Tzur |
| 2009/0083054 A1 | 3/2009 | Koo |
| 2009/0119170 A1 | 5/2009 | Hammad |
| 2009/0144122 A1 | 6/2009 | Ginsberg |
| 2009/0261974 A1 | 10/2009 | Bailey |
| 2009/0322481 A1 | 12/2009 | Marr, III |
| 2010/0006646 A1 | 1/2010 | Stiller |
| 2010/0007464 A1 | 1/2010 | Mctigue |
| 2010/0042369 A1 | 2/2010 | Mian |
| 2010/0065632 A1 | 3/2010 | Babcock |
| 2010/0101317 A1 | 4/2010 | Ashrafzadeh |
| 2010/0111354 A1 | 5/2010 | Hornabrook |
| 2010/0138281 A1 | 6/2010 | Zhang |
| 2010/0253504 A1 | 10/2010 | Lliteras |
| 2011/0029413 A1 | 2/2011 | Ben-Tzur |
| 2011/0035326 A1 | 2/2011 | Sholl |
| 2011/0068921 A1 | 3/2011 | Shafer |
| 2011/0301903 A1 | 12/2011 | Humbert |
| 2012/0101876 A1 | 4/2012 | Turvey |
| 2012/0161967 A1 | 6/2012 | Stern |
| 2012/0264446 A1 | 10/2012 | Xie |
| 2012/0267541 A1 | 10/2012 | Utukuri |
| 2012/0304014 A1 | 11/2012 | Prophete |
| 2012/0310853 A1 | 12/2012 | Aldstadt |
| 2013/0002443 A1 | 1/2013 | Breed |
| 2013/0117053 A2 | 5/2013 | Campbell |
| 2013/0176115 A1 | 7/2013 | Puleston |
| 2013/0214797 A1 | 8/2013 | Gruden |
| 2013/0218511 A1 | 8/2013 | Mager |
| 2013/0235206 A1 | 9/2013 | Smith |
| 2013/0282522 A1 | 10/2013 | Hassan |
| 2014/0138440 A1 | 5/2014 | D'Ambrosio |
| 2014/0146164 A1 | 5/2014 | Bajema |
| 2014/0147015 A1 | 5/2014 | Bajema |
| 2014/0180953 A1 | 6/2014 | Westcott |
| 2014/0201041 A1 | 7/2014 | Meyer |
| 2014/0294239 A1 | 10/2014 | Duckett |
| 2014/0297487 A1 | 10/2014 | Bashkin |
| 2014/0313055 A1 | 10/2014 | Warkentin |
| 2014/0316875 A1 | 10/2014 | Tkachenko |
| 2014/0330407 A1 | 11/2014 | Corder |
| 2015/0015373 A1 | 1/2015 | Mongrenier |
| 2015/0019391 A1 | 1/2015 | Kumar |
| 2015/0021401 A1 | 1/2015 | Rajagopal |
| 2015/0022313 A1 | 1/2015 | Maier |
| 2015/0041616 A1 | 2/2015 | Gentile |
| 2015/0048938 A1 | 2/2015 | Tew |
| 2015/0084100 A1 | 3/2015 | Sablong |
| 2015/0095255 A1 | 4/2015 | Hall |
| 2015/0102903 A1 | 4/2015 | Wilkinson |
| 2015/0186840 A1 | 7/2015 | Torres |
| 2015/0192475 A1 | 7/2015 | Eisenstadt |
| 2015/0245179 A1 | 8/2015 | Jarvis |
| 2015/0338846 A1 | 11/2015 | Boivin |
| 2015/0347945 A1 | 12/2015 | Reese |
| 2015/0349917 A1 | 12/2015 | Skaaksrud |
| 2016/0012337 A1 | 1/2016 | Kaye |
| 2016/0026032 A1 | 1/2016 | Moore |
| 2016/0033194 A1* | 2/2016 | Sumihiro ............... F25D 23/04 62/125 |
| 2016/0034907 A1 | 2/2016 | Worrall |
| 2016/0048798 A1 | 2/2016 | Meyer |
| 2016/0063367 A1 | 3/2016 | Cai |
| 2016/0132821 A1 | 5/2016 | Glasgow |
| 2016/0148440 A1 | 5/2016 | Kwak |
| 2016/0171434 A1 | 6/2016 | Ladden |
| 2016/0189087 A1 | 6/2016 | Morton |
| 2016/0203591 A1 | 7/2016 | Justaniah |
| 2016/0217417 A1* | 7/2016 | Ma ......................... H04N 5/225 |
| 2016/0239794 A9 | 8/2016 | Shafer |
| 2016/0260059 A1 | 9/2016 | Benjamin |
| 2016/0283904 A1 | 9/2016 | Siegel |
| 2016/0292634 A1 | 10/2016 | Mehring |
| 2016/0307040 A1 | 10/2016 | Shulman |
| 2016/0314514 A1 | 10/2016 | High |
| 2016/0350715 A1 | 12/2016 | Minvielle |
| 2016/0350756 A1 | 12/2016 | Shepard |
| 2017/0039194 A1 | 2/2017 | Tschetter |
| 2017/0039511 A1 | 2/2017 | Corona |
| 2017/0059391 A1 | 3/2017 | Ademe |
| 2017/0061171 A1 | 3/2017 | Lombardi |
| 2017/0061394 A1 | 3/2017 | High |
| 2017/0074921 A1 | 3/2017 | Uota |
| 2017/0102694 A1 | 4/2017 | Enver |
| 2017/0116565 A1 | 4/2017 | Feiner |
| 2017/0122771 A1 | 5/2017 | Keal |
| 2017/0164773 A1 | 6/2017 | Wirtz |
| 2017/0255901 A1 | 9/2017 | Bermudez Rodriguez |
| 2017/0269601 A1 | 9/2017 | Jones |
| 2017/0280351 A1 | 9/2017 | Skaaksrud |
| 2017/0286905 A1 | 10/2017 | Richardson |
| 2017/0300984 A1 | 10/2017 | Hurwich |
| 2017/0322090 A1 | 11/2017 | Jones |
| 2017/0344934 A1 | 11/2017 | Millhouse |
| 2017/0344935 A1 | 11/2017 | Mattingly |
| 2018/0007453 A1 | 1/2018 | Taylor |
| 2018/0039853 A1 | 2/2018 | Liu |
| 2018/0045700 A1 | 2/2018 | Biermann |
| 2018/0078992 A1 | 3/2018 | High |
| 2018/0096175 A1 | 4/2018 | Schmeling |
| 2018/0137642 A1 | 5/2018 | Malisiewicz |
| 2018/0143131 A1 | 5/2018 | Choi |
| 2018/0144300 A1 | 5/2018 | Wiechers |

(56) References Cited

U.S. PATENT DOCUMENTS

| | | |
|---|---|---|
| 2018/0144430 A1 | 5/2018 | Millhouse |
| 2018/0150684 A1 | 5/2018 | Wang |
| 2018/0168054 A1 | 6/2018 | Scarlata |
| 2018/0180492 A1 | 6/2018 | Ribi |
| 2018/0181838 A1 | 6/2018 | Yang |
| 2018/0195869 A1 | 7/2018 | High |
| 2018/0211208 A1 | 7/2018 | Winkle |
| 2018/0217118 A1 | 8/2018 | Payne |
| 2018/0242768 A1 | 8/2018 | Lewis |
| 2018/0247257 A1 | 8/2018 | Lert, Jr. |
| 2018/0270631 A1 | 9/2018 | High |
| 2018/0279023 A1 | 9/2018 | Taylor |
| 2018/0290809 A1 | 10/2018 | Espinosa |
| 2018/0315011 A1 | 11/2018 | Clarke |
| 2018/0341905 A1 | 11/2018 | Johnsen |
| 2019/0073770 A1 | 3/2019 | Moradi |
| 2019/0147396 A1 | 5/2019 | Bohling |
| 2019/0223643 A1 | 7/2019 | Hara |
| 2019/0285603 A1 | 9/2019 | Velez |
| 2020/0034962 A1 | 1/2020 | Mathew |
| 2020/0085290 A1 | 3/2020 | Wang |
| 2020/0118072 A1 | 4/2020 | Johnson |
| 2020/0160497 A1 | 5/2020 | Shah |
| 2020/0242402 A1 | 7/2020 | Jung |
| 2020/0275010 A1 | 8/2020 | Bohling |
| 2021/0398065 A1 | 12/2021 | Johnsen |
| 2022/0010160 A1 | 1/2022 | Zhong |

FOREIGN PATENT DOCUMENTS

| | | |
|---|---|---|
| CN | 201314907 | 9/2009 |
| CN | 202306566 | 7/2012 |
| CN | 102930649 | 2/2013 |
| CN | 203275285 | 11/2013 |
| CN | 203306566 | 11/2013 |
| CN | 103543703 | 1/2014 |
| CN | 103593746 | 2/2014 |
| CN | 104036354 | 9/2014 |
| CN | 204010264 | 12/2014 |
| CN | 104749329 | 7/2015 |
| CN | 204514846 | 7/2015 |
| CN | 204989059 | 1/2016 |
| CN | 105444504 | 3/2016 |
| CN | 106408173 | 2/2017 |
| CN | 106600286 | 4/2017 |
| CN | 107703269 | 2/2018 |
| EP | 1221613 | 7/2002 |
| EP | 1374688 | 1/2004 |
| EP | 2165298 | 3/2010 |
| EP | 2509412 | 10/2012 |
| EP | 2509412 A1 | 10/2012 |
| EP | 2835078 | 2/2015 |
| GB | 2256708 | 12/1992 |
| JP | 2002195971 A | 7/2002 |
| JP | 2008004133 | 1/2008 |
| JP | 2008004133 A | 1/2008 |
| JP | 2013068547 | 4/2013 |
| WO | 2000078919 A1 | 12/2000 |
| WO | 2001023256 | 4/2001 |
| WO | 2003098175 | 11/2003 |
| WO | 2007052208 A1 | 5/2007 |
| WO | 2008006152 A1 | 1/2008 |
| WO | 2008016309 | 2/2008 |
| WO | 2008147897 | 12/2008 |
| WO | 2009147821 A1 | 12/2009 |
| WO | 2012125960 | 9/2012 |
| WO | 2013174983 | 11/2013 |
| WO | 2014059048 | 4/2014 |
| WO | 2015061429 | 4/2015 |
| WO | 2015066594 | 5/2015 |
| WO | 2020023762 | 1/2020 |

OTHER PUBLICATIONS

IBM; "Focus on Food Safety"; https://www.ibm.com/downloads/cas/ZN9EWKRQ; Available at least as early as 2018; pp. 1-2.

Mitrokotsa et al.; "Integrated RFID and Sensor Networks: Architectures and Applications"; https://pdfs.semanticscholar.org/e5b0/c2a44971bad209cbf66afb6c825f89792723.pdf; Jun. 22, 2009; pp. 511-536.

PCT; App. No. PCT/US2019/043849; International Search Report and Written Opinion dated Dec. 3, 2019.

United States Army Medical Command; "U.S. Army Veterinary Command Guidelines and Procedures"; https://www.dla.mil/Portals/104/Documents/TroopSupport/Subsistence/Rations/qapub s/medcom/40-13.pdf; Feb. 13, 2006; pp. 1-171.

3M; "3M MonitorMark Time Temperature Indicators"; https://www.3m.com/3M/en_US/company-us/all-3m-products/~/MONMARK-3M-MonitorMark-Time-Temperature-Indicators/?N=5002385+3293785721&rt=rud; Available at least as early as Feb. 7, 2019; pp. 1-4.

Agrofresh; "FreshCloud™ Storage Insights helps you monitor fruit in storage for added peace of mind"; https://www.agrofresh.com/technologies/freshcloud/storage-insights/; Available at least as early as Feb. 7, 2019; pp. 1-4.

Ahearn, Brianna; "Kroger Wins For Food Temperature Innovation"; https://www.retailsupplychaininsights.com/doc/kroger-wins-for-food-temperature-innovation-0001; Jun. 4, 2015; pp. 1-2.

Ambrosus; "Decentralised IoT Networks for Next-Generation Supply Chains"; https://ambrosus.com/#home; Available at least as early as Feb. 7, 2019; pp. 1-12.

Anzilotti, Eillie; "These High-Tech Sensors Track Exactly How Fresh Our Produce Is So We Stop Wasting Food"; https://www.fastcompany.com/40424163/these-high-tech-sensors-track-exactly-how-fresh-our-produce-is-so-we-stop-wasting-food; May 26, 2017; pp. 1-3.

Bedard, Jean; "Temperature Mapping of Storage Areas"; Technical supplement to WHO Technical Report Series, No. 961, 2011; WHO Press, World Health Organization; available at least as early as Jan. 2014; pp. 1-25.

BT9 Intelligent Supply Chain Solutions; "Multi Segment, Real Time, Cold Chain Perishable Information"; http://www.bt9-tech.com; Published 2018; pp. 1-6.

Business Wire; "Emerson Expands Global Capabilities in Fresh Food Monitoring with Acquisitions of Locus Traxx and PakSense"; https://www.businesswire.com/news/home/20160830005136/en/Emerson-Expands-Global-Capabilities-Fresh-Food-Monitoring; Aug. 30, 2016; pp. 1-2.

Cao, Jordan; "Intelligent Container—powered by SAP HANA"; https://blogs.saphana.com/2018/09/27/intelligent-container-powered-sap-hana/; Sep. 27, 2018; pp. 1-5.

Carrefour Group; "Carrefour launches Europe's first food blockchain"; http://www.carrefour.com/current-news/carrefour-launches-europes-first-food-blockchain; Mar. 6, 2018; pp. 1-2.

Compact.net; "Inspection Planning / Quality Inspection / SPC / LIMS"; https://www.caq.de/en/Software/InspectionPlanning_QualityInspection_SPC; available at least as early as Jan. 27, 2017; pp. 1-4.

De Troch, Stefan; "Item-level cold chain monitoring, another cool NFC solution"; https://blog.nxp.com/internet-of-things-2/item-level-cold-chain-monitoring-another-cool-nfc-solution; Aug. 30, 2016; pp. 1-5.

Digi; "Digi Honeycomb Keeping food safe just got easier and cheaper. Digi Honeycomb lets you monitor your entire Cold Chain System"; https://s3.amazonaws.com/telusdigital-marketplace-production/iot/user-content/product/64aa-o.pdf; Available at least as early as Feb. 7, 2019; pp. 1-2.

Dji Ferntech; "Drones For Agriculture"; https://www.djistore.co.nz/agriculture; Available at least as early as Feb. 7, 2019; pp. 1-13.

Ecoark Holdings, Inc.; "Ocean Mist Farms Selects Zest Fresh to Optimize Freshness Management"; https://www.globenewswire.com/news-release/2018/12/04/1661680/0/en/Ocean-Mist-Farms-Selects-Zest-Fresh-to-Optimize-Freshness-Management.html; Dec. 4, 2018; pp. 1-3.

(56) References Cited

OTHER PUBLICATIONS

Emerson; "ProAct Services and ProAct Transport"; https://www.emerson.com/en-us/commercial-residential/proact; Available at least as early as Feb. 7, 2019; pp. 1-4.
Emerson; "Real-Time Temperature & Location Trackers"; https://climate.emerson.com/en-us/products/controls-monitoring-systems/cargo-tracking-monitoring/trackers; Available at least as early as Feb. 7, 2019; pp. 1-4.
Emerson; "Supply Chain Data Loggers"; https://climate.emerson.com/en-us/products/controls-monitoring-systems/cargo-tracking-monitoring/loggers; Available at least as early as Feb. 7, 2019; pp. 1-4.
Eom, Ki-Hwan, et al.; "The Meat Freshness Monitoring System Using the Smart RFID Tag"; International Journal of Distributed Sensor Networks, vol. 2014; http://journals.sagepub.com/doi/10.1155/2014/591812; Jul. 9, 2014; pp. 1-10.
Fast Casual; "Wireless temperature-monitoring, tracking solution available for shipping perishable goods"; https://www.fastcasual.com/news/wireless-temperature-monitoring-and-tracking-solution-now-available-for-shipping-perishable-goods/; Aug. 15, 2017; pp. 1-10.
Food and Agriculture Organization of the United Nations; "Flying robots for food security"; http://www.fao.org/zhc/detail-events/en/c/428256; Aug. 10, 2016; pp. 1-3.
Freshai; "AI-powered waste reduction for smart food businesses."; http://freshai.farmsteadapp.com/; Available as early as Feb. 7, 2019; pp. 1-5.
Freshfruitportal.com; "Zest Labs fights food waste by routing pallets according to real-time freshness"; https://www.freshfruitportal.com/news/2018/07/19/technology-zest-labs-food-waste-profits-sensors; Jul. 19, 2018; pp. 1-5.
Friedman, Phil; "AI, machine learning, and more efficient routing"; https://www.omnitracs.com/blog/ai-machine-learning-and-more-efficient-routing; Jun. 28, 2018; pp. 1-6.
Gabbett, Rita Jane; "Amazon using artificial intelligence to monitor food safety issues"; http://www.micausa.org/amazon-using-artificial-intelligence-monitor-food-safety-issues/; May 9, 2018; pp. 1-3.
Grand View Research; "Cold Chain Market Size Worth $447.50 Billion By 2025 | CAGR: 15.1%"; https://www.grandviewresearch.com/press-release/global-cold-chain-market; Mar. 2019; pp. 1-10.
Greenwalt, Megan; "Acquisition Leads to New, Fresh Food Waste Solution"; https://www.waste360.com/mergers-and-acquisitions/acquisition-leads-new-fresh-food-waste-solution; Aug. 15, 2018; pp. 1-6.
Greis, Noel P.; "Monitoring the 'Cool Chain' Maximizing Shelf Life for Safer Food"; https://atecentral.net/r20093/case_study_monitoring_the_cool_chain; National Science Foundation; published on Dec. 2011; pp. 1-9.
Hagen, Christian et al.; "A Fresh Look: Perishable Supply Chains Go Digital"; https://www.atkearney.com/operations-performance-transformation/article?/a/a-fresh-look-perishable-supply-chains-go-digital; Available at least as early as Feb. 7, 2019; pp. 1-22.
Harvard Business Review; "How Blockchain Will Accelerate Business Performance and Power the Smart Economy"; https://hbr.org/sponsored/2017/10/how-blockchain-will-accelerate-business-performance-and-power-the-smart-economy; Oct. 27, 2017; pp. 1-8.
Hsu, Jenny W.; "Freshippo Customers Can Track Farm-to-Shelf Journey for Food"; https://www.alizila.com/hema-food-tracking/; Aug. 7, 2018; pp. 1-6.
Husseini, Talal; "Walmart's 'Eden' artificial intelligence technology to inspect fresh food for spoilage"; https://www.foodprocessing-technology.com/news/walmarts-eden-artificial-intelligence-technology-inspect-fresh-food-spoilage; Mar. 2, 2018; pp. 1-4.
IBM; "Take your food data further with Fresh Insights for IBM Food Trust"; https://www.ibm.com/blockchain/solutions/food-trust/freshness; Available at least as early as Feb. 7, 2019; pp. 1-3.
Impact Vision; "Non-invasive, real time food quality information"; https://www.impactvi.com/; Available at least as early as Feb. 7, 2019; pp. 1-18.
Impinj; "Hy-Vee Grocery Automates Cold Chain Monitoring"; https://www.impinj.com/library/customer-stories/hy-vee-cold-chain-monitoring-increases-shelf-life/; Available as early as Feb. 7, 2019; pp. 1-3.
Infratab; "Products"; https://infratab.com/products/; Available at least as early as Feb. 7, 2019; pp. 1-2.
Intel; "Intelligent Dynamic Store Merchandising Solution Cuts Losses on Perishables and Raises Brand Awareness"; Available at least as early as Feb. 7, 2019; pp. 1-12.
IQA Team; "Material Inspection Using a Cloud Software"; http://Mqalims.com/wp-content/uploads/2015/02/MAT_INSP.pdf; available at least as early as Jan. 27, 2017; pp. 1-5.
Jedermann, Reiner, et al.; "Semi-passive RFID and Beyond: Steps Towards Automated Quality Tracing in the Food Chain"; Inderscience Enterprises Ltd.; Int. J. Radio Frequency Identification Technology and Applications, vol. 1, No. 3; published in 2007; pp. 247-259.
Kroger; "Kroger Gets HarvestMark Allows consumers to trace the origin of salads"; https://www.cspdailynews.com/foodservice/kroger-gets-harvestmark; Oct. 29, 2009; pp. 1-11.
Marvin, Rob; "Blockchain: The Invisible Technology That's Changing the World"; https://in.pcmag.com/amazon-web-services/112363/blockchain-the-invisible-technology-thats-changing-the-world; Aug. 30, 2017; pp. 1-29.
Mazur, Michal; "Six Ways Drones Are Revolutionizing Agriculture"; https://www.technologyreview.com/s/601935/six-ways-drones-are-revolutionizing-agriculture; Jul. 20, 2016; pp. 1-5.
Mipsis; "Quality Control Inspection Software"; http://www.mipsis.com/QualityInspectionSoftware.html; available at least as early as Jan. 27, 2017; pp. 1-3.
Moorthy, Rahul et al.; "On-Shelf Availability in Retailing"; vol. 116—No. 23; International Journal of Computer Applications; Apr. 2015; pp. 47-51.
Moorthy, Rahul, et al.; "On-Shelf Availability in Retailing"; vol. 116—No. 23; International Journal of Computer Applications; available at least as early as Apr. 2015; pp. 47-51.
Musani, Parvez; "Eden: The Tech That's Bringing Fresher Groceries to You"; https://blog.walmart.com/innovation/20180301/eden-the-tech-thats-bringing-fresher-groceries-to-you; Mar. 1, 2018; pp. 1-4.
My Devices; "Alibaba Cloud and myDevices Partner to Launch Turnkey IoT Solutions in China"; https://mydevices.com/newspost/alibaba-cloud-mydevices-partner-launch-turnkey-iot-solutions-china/; Sep. 11, 2018; pp. 1-3.
Oracle; "Oracle Unveils Business-Ready Blockchain Applications"; https://www.oracle.com/nz/corporate/pressrelease/oow18-oracle-blockchain-applications-cloud-2018-10-23.html; Oct. 23, 2018; pp. 1-4.
Palanza, Rich; "IoT Monitoring: Rapidly Deliver on the Promise of IoT"; https://business.weather.com/blog/iot-monitoring-rapidly-deliver-on-the-promise-of-iot; May 16, 2018; pp. 1-4.
Peterson, Hayley; "Walmart is saving $2 billion with a machine called 'Eden' that inspects food and knows when it will spoil"; https://www.businessinsider.in/walmart-is-saving-2-billion-with-a-machine-called-eden-that-inspects-food-and-knows-when-it-will-spoil/articleshow/63127641.cms; Mar. 1, 2018; pp. 1-12.
Pridevel; "IoT Cold Chain Monitoring"; http://www.pridevel.com/sap-iot-cold-chain-monitoring; Available at least as early as Feb. 7, 2019; pp. 1-3.
QA; "Carrefour and SGS Launch Visual Trust in China"; https://www.qualityassurancemag.com/article/carrefour-and-sgs-launch-visual-trust-in-china/; Sep. 28, 2017; pp. 1-4.
QC One; "Inspect. Report. Analyze. Quality Control Software for Fresh Produce"; http://qcone.com/en/; available at least as early as May 29, 2017; pp. 1-2.
Ripple News Tech Staff; "Alibaba is Using Blockchain to Improve Consumer Confidence and Fight Food Fraud"; https://ripplenews.tech/2018/05/03/alibaba-is-using-blockchain-to-improve-consumer-confidence-and-fight-food-fraud/; May 3, 2018; pp. 1-7.
Ryan, John M.; "Guide to Food Safety and Quality During Transportation: Controls, Standards and Practices"; Academic Press; available at least as early as 2014; pp. 1-8.

(56) References Cited

OTHER PUBLICATIONS

Sensefly; "Why Use Agriculture Drones?"; https://www.sensefly.com/industry/agricultural-drones-industry; Available at least as early as Feb. 7, 2019; pp. 1-15.
Sensegrow; "Supply Chain Monitoring with Real-time IoT Platform"; http://www.sensegrow.com/blog/supply-chain-monitoring; May 10, 2018; pp. 1-5.
Smart Sense; "Supermarket Remote Monitoring Solutions"; https://www.smartsense.co/industries/retail/supermarkets; Available at least as early as Feb. 7, 2019; pp. 1-6.
Smilo; "The latest generation hybrid blockchain platform"; https://smilo.io/files/Smilo_White_Paper_V1.8.1.pdf; Available at least as early as Feb. 7, 2019; pp. 1-33.
Softexpert; "SE Inspection Incoming/Outgoing Goods Inspection and Supplier Management"; https://softexpert.com/inspection-evaluation-goods.php; available at least as early as Jan. 27, 2017; pp. 1-3.
Springer, Jon; "Walmart, Kroger join suppliers in blockchain food safety initiative"; https://www.supermarketnews.com/news/walmart-kroger-join-suppliers-blockchain-food-safety-initiative; Aug. 22, 2017; pp. 1-4.
TCS Worldwide; "TCS Cargo Monitoring Solution: Track freshness of perishable cargo"; https://www.tcs.com/cargo-monitoring-solution; Available at least as early as Feb. 7, 2019; pp. 1-7.
TE-Food; "TE-Food Partners with Halal Trail Bringing Halal Food Companies to the Blockchain"; https://www.reuters.com/brandfeatures/venture-capital/article?id=38153; May 31, 2018; pp. 1-6.
Tech Mahindra; "Cold Chain Monitoring"; https://www.techmahindra.com/services/NextGenSolutions/DES/Solutions/Cold_Chain_Monitoring.aspx; Available at least as early as Feb. 7, 2019; pp. 1-4.
Tech Mahindra; "Farm to fork"; https://www.techmahindra.com/services/NextGenSolutions/DES/Solutions/Farm_to_fork.aspx; Available at least as early as Feb. 7, 2019; pp. 1-2.
Teijin—Human Chemistry, Human Solutions, Teijin's RFID Smart Shelf-Management System Used for Mass Document Management. Retrieved online at: http://www.teijin.com/news/2014/ebd140307_11.html. 2 pages, Mar. 7, 2014.
The NeWave® Smart Inventory Managment System: Take Your Management to the Next Level, NeWave Sensor Solutions Innovation Center, Oct. 7, 2016; pp. 1-2.
Tive; "A Complete Supply Chain Visibility System"; https://tive.co/product; Available at least as early as Feb. 7, 2019; pp. 1-7.
Tive; "Environmental Monitoring for Perishables"; https://tive.co/solution/environmental-monitoring-for-perishables/; Available at least as early as Feb. 7, 2019; pp. 1-5.
Traqtion; "TraQtion's Supply Chain Solution Manages Global Food Supplier Compliance and Audits"; https://www.traqtion.com/documents/TraQtion-Costco.pdf; Available as early as Feb. 7, 2019; pp. 1-2.
Trimble; "Trimble Acquires HarvestMark to Provide Food Traceability and Quality Control"; https://www.prnewswire.com/news-releases/trimble-acquires-harvestmark-to-provide-food-traceability-and-quality-control-300070050.html; Apr. 22, 2015; pp. 1-6.
Tsenso; "The Fresh Index: A Real-Time Shelf Life Indicator"; https://tsenso.com/en/freshindex-instead-of-bestbefore; Available at least as early as Feb. 7, 2019; pp. 1-5.
Verigo; "Introducing Pod Quality Continuous Product Life Data, From Farm to Store"; https://www.farmtoforkfresh.com/; Available at least as early as Feb. 7, 2019; pp. 1-8.
Wageningen Ur Food & Biobased Research; "Food & Biobased Research"; https://www.worldfoodinnovations.com/userfiles/documents/FBR%20Corporate%20Brochure.pdf; Jul. 2014; pp. 1-24.
Whelan, Jenny; "Kelsius To Install FoodCheck Monitoring System In Supervalu And Centra Stores"; https://www.checkout.ie/kelsius-signs-deal-to-put-foodcheck-monitoring-system-in-supervalu-and-centra-stores/; Aug. 6, 2015; pp. 1-4.
Wynne-Jones, Stephen; "Maxima Group Unveils Electronic Nose' To Track Freshness"; https://www.esmmagazine.com/maxima-group-unveils-elecrtronic-nose-track-freshness/29589; Jul. 5, 2016; pp. 1-4.
Xinfin; "Enterprise Ready Hybrid Blockchain for Global Trade and Finance"; https://www.xinfin.org; Available at least as early as Feb. 7, 2019; pp. 1-13.
Yan, Lu, et al.; "The Internet of Things: From RFID to the Next-Generation Pervasive Networked Systems"; Auerbach Publications; New York; available at least as early as 2008; pp. 1-35.
Yiannas, Frank; "How Walmart's SPARK Keeps Your Food Fresh"; https://blog.walmart.com/sustainability/20150112/how-walmarts-spark-keeps-your-food-fresh; Jan. 12, 2015; pp. 1-16.
Zest Labs; "Zest Fresh for Growers, Retailers and Restaurants"; https://www.zestlabs.com/zest-fresh-for-produce/; Available at least as early as Feb. 7, 2019; pp. 1-7.
Arah, Isaac Kojo et al.; "Preharvest and Postharvest Factors Affecting the Quality and Shelf Life of Harvested Tomatoes: A Mini Review"; http://downloads.hindawi.com/journals/ija/2015/478041.pdf; Available as early as Oct. 14, 2015; pp. 1-7.
Badia, Ricardo; "Cold Chain Logistics: Assessing the Challenge"; https://www.zestlabs.com/assessing-cold-chain-logistics/; Mar. 19, 2019; pp. 1-4.
Barthe, J.F.; "D.2.3.2. Database of consumer awareness, expectations and concerns on cold chain"; http://www.frisbee-project.eu/images/result/FRISBEE_DEL_2-3-2.pdf; Dec. 2, 2011; pp. 1-26.
Barthe, J.F.; "D.2.3.2.1 Survey questionnaires and materials for studies of consumer perspectives and attitudes towards refrigerated foods, the cold chain and relevant refrigeration technologies (Informed consent forms, privacy, personal data handling)"; http://www.frisbee-project.eu/images/result/FRISBEE_DEL_2-3-2-1.pdf; Feb. 8, 2012; pp. 1-21.
Bogataj, M., et al.; "Stability of perishable goods in cold logistic chains"; International Journal of Production Economics, vol. 93-94; 2005; pp. 345-356.
Capgemini; "Schuitema Revolutionizes Food Quality Control Through RFID"; https://www.capgemini.com/se-en/wp-content/uploads/sites/29/2017/07/Schuitema_Revolutionizes_Food_Quality_Control_Through_RFID.pdf; Jul. 29, 2017; pp. 1-2.
Chainlink Research; "Achieving Consistent Product Quality"; https://www.zestlabs.com/wp-content/uploads/2016/12/Quality-Management-For-Produ ce.pdf; Available as early as Dec. 2016; pp. 1-8.
Chainlink Research; "Measuring Produce Freshness: The Key to Preventing Waste"; https://www.zestlabs.com/wp-content/uploads/2016/03/Measuring-Produce-Freshness. pdf; Available as early as Mar. 2016; pp. 1-12.
Chainlink Research; "Preemptive Freshness Management"; https://www.zestlabs.com/wp-content/uploads/2017/03/Preemptive-Freshness-Managem ent.pdf; Available as early as Mar. 2017; pp. 1-8.
Chainlink Research; "Blockchain's Role in the Produce Supply Chain"; https://www.zestlabs.com/wp-content/uploads/2018/01/Blockchains-Role-in-the-Prod uce-Supply-Chain.pdf; Available as early as Jan. 2018; pp. 1-20.
Chainlink Research; "Pallet-level Monitoring"; https://www.zestlabs.com/wp-content/uploads/2016/03/Pallet-Monitoring-for-the-Fr esh-Food-Supply-Chain.pdf; Available as early as Mar. 2016; pp. 1-9.
Chainlink Research; "Why Quality Consistency Matters"; https://www.zestlabs.com/wp-content/uploads/2016/03/Why-Food-Supply-Chain-Qualit y-Matters-1.pdf; Available as early as Mar. 2016; pp. 1-10.
Claussen, Ingrid C.; "Deliverable D.3.2.4.3 Literature review and experimental data of chilled, superchilled/supercooled fish quality and safety models"; http://www.frisbee-project.eu/images/result/FRISBEE_DEL_3-2-4-3.pdf; May 6, 2011; pp. 1-29.
Colmer, Christian; "Chill—ON! Transparent food quality all the way"; https://www.innovations-report.com/html/reports/medicine-health/chill-transparen t-food-quality-168201.html; Oct. 1, 2011; pp. 1-5.
Cotillon, C.; "Deliverable 8.2.1.1 Publication in Scientific Journals"; http://www.frisbee-project.eu/images/result/FRISBEE_DEL_8.2.1.1.pdf; Oct. 27, 2011; pp. 1-5.
Cotillon, C.; "Deliverable 8.3.3.1 Mini conferences"; http://www.frisbee-project.eu/images/result/FRISBEE_DEL_8.3.3.1.pdf; Dec. 7, 2011; pp. 1-8.
Cotillon, C.; "Deliverable 8.6.1 Report on collaboration with other EU projects"; http://www.frisbee-project.eu/images/result/FRISBEE_DEL_8.6.1.pdf; Dec. 5, 2011; pp. 1-12.

(56) References Cited

OTHER PUBLICATIONS

Dada, Ali, et al.; "Sensor Applications in the Supply Chain: The Example of Quality-Based Issuing of Perishables"; The Internet of Things. Lecture Notes in Computer Science, edited by Christian Floerkemeier, et al.; vol. 4952; 2008; pp. 140-154.
Desmedt, Frederique; "Deliverable 8.1.1 Project logo, Leaflet and PowerPoint presentation"; http://www.frisbee-project.eu/images/result/FRISBEE_DEL_8.1.1.pdf; Nov. 19, 2010; pp. 1-30.
Desmedt, Frederique; "Deliverable 8.1.2 Project internet and intranet website"; http://www.frisbee-project.eu/images/result/FRISBEE_DEL_8.1.2.pdf; Mar. 3, 2011; pp. 1-9.
Do Nascimento Nunes, M. C., et al.; "Improvement in fresh fruit and vegetable logistics quality: berry logistics field studies"; Philosophical Transactions of the Royal Society; http://dx.doi.org/10.1098/rsta.2013.0307; 2014; pp. 1-19.
Doyle, John P.; "Seafood Shelf Life as a Function of Temperature"; Alaska Sea Grant Marine Advisory Program; No. 30; 1989; pp. 1-6.
Evans, J.; "Deliverable D2.2.2 : Assessment of current refrigeration technologies of selected food industries and their potential improvement in current refrigeration"; http://www.frisbee-project.eu/images/result/FRISBEE_DEL_2-2-2.pdf; Jan. 30, 2012; pp. 1-181.
Evans, Judith et al.; "Deliverable D.2.2.3 : Analysis of potential of novel refrigeration technologies suitable for selected industries for application and improvement of food quality, energy consumption and environmental impact"; http://www.frisbee-project.eu/images/result/FRISBEE_DEL_2-2-3.pdf; Dec. 2, 2011; pp. 1-54.
Friedlos, Dave; "New Zealand Kiwifruit Processor Finds ROI"; https://www.rfidjournal.com/articles/view?4090; May 20, 2008; pp. 1-4.
Frisbee; "Frisbee european project—Archive"; https://web.archive.org/web/20180815100417/http://www.frisbee-project.eu/archive-results.html; Available as early as Aug. 15, 2018; pp. 1-5.
Frisbee; "Frisbee european project—Developing novel breakthrough technologies"; https://web.archive.org/web/20180316101206/http://www.frisbee-project.eu/researc h/92-developing-novel-breakthrough-technologies.html; Available as early Mar. 16, 2018; pp. 1-3.
Frisbee; "Frisbee european project—Frisbee at the Sixteenth Conference on Food Microbiology, Belgium"; http://www.frisbee-project.eu/news/40-frisbee-at-the-sixteenth-conference-on-foo d-microbiology.html; Nov. 15, 2011; pp. 1-1.
Frisbee; "Frisbee european project—Frisbee develops a Virtual Platform application"; http://www.frisbee-project.eu/news/90-frisbee-develops-a-virtual-platform-applic ation.html; Mar. 18, 2013; pp. 1-1.
Frisbee; "Frisbee european project—Frisbee dissemination activities"; http://www.frisbee-project.eu/news/91-frisbee-dissemination-activities.html; Mar. 18, 2013; pp. 1-1.
Frisbee; "Frisbee european project—Frisbee on the starting-blocks"; http://www.frisbee-project.eu/news/49-frisbee-on-the-starting-blocks.html; Mar. 9, 2012; pp. 1-2.
Frisbee; "Frisbee european project—Frisbee welcomes New Members Advisory Board"; http://www.frisbee-project.eu/news/48-new-members-advisory-board.html; Mar. 9, 2012; pp. 1-1.
Frisbee; "Frisbee european project—Frisbee: Latest Developments"; http://www.frisbee-project.eu/news/42-frisbee-project-latest-developments.html; Dec. 21, 2011; pp. 1-2.
Frisbee; "Frisbee european project—Join the first European Food Cold Chain Database!!!";http://www.frisbee-project.eu/news/55-database2.html; Jul. 9, 2012; pp. 1-2.
Frisbee; "Frisbee european project—Magnetic refrigeration technology. Frisbee's experts team work on this disruptive technology"; https://web.archive.org/web/20180316101206/http://www.frisbee-project.eu/researc h/51-magnetic-refrigeration-technology.html; Available as early as Mar. 16, 2018; pp. 1-3.
Frisbee; "Frisbee european project—MEP-scientist pairing scheme"; http://www.frisbee-project.eu/news/41-mep-scientist-pairing-scheme.html; Dec. 20, 2011; pp. 1-2.
Frisbee; "Frisbee european project—Nanoparticles, a concentrate of energy: PCM nanoparticles where low temperatures are needed"; https://web.archive.org/web/20180316101206/http://www.frisbee-project.eu/researc h/27-nanoparticles-a-concentrate-of-energy.html; Available as early as Mar. 16, 2018; pp. 1-2.
Frisbee; "Frisbee european project—Project Overview"; https://web.archive.org/web/20120211082956/http://www.frisbee-project.eu/project-overview.html; Available as early as Feb. 11, 2012; pp. 1-1.
Frisbee; "Frisbee european project—Saving energy by refrigeration predictive control"; https://web.archive.org/web/20180316101206/http://www.frisbee-project.eu/researc h/52-saving-energy-by-refrigeration-predictive-control.html; Available as early as Mar. 16, 2018; pp. 1-3.
Frisbee; "Frisbee european project—Superchilling! A new technology to have your food products fresher than fresh"; https://web.archive.org/web/20180316101206/http://www.frisbee-project.eu/researc h/50-superchilling.html; Available as early as Mar. 16, 2018; pp. 1-3.
Frisbee; "Frisbee european project—Taking Europe's temperature: Cold chain database"; http://www.frisbee-project.eu/news/89-taking-europe%E2%80%99s-temperature-cold-c hain-database.html; Mar. 18, 2013; pp. 1-2.
Frisbee; "Frisbee european project—Workpackages"; https://web.archive.org/web/20120210124516/http://www.frisbee-project.eu/workpac kages.html; Available as early as Feb. 10, 2012; pp. 1-2.
Frisbee; "Simulate a cold chain"; https://frisbee-etool.irstea.fr; Available as early as 2020; pp. 1-3.
Gapud, Veny; "Food Safety Trends Exploring Implications of Mandatory Safety Standards in Retail and Foodservice"; https://www.foodsafetymagazine.com/magazine-archive1/december-2009january-2010/f ood-safety-trends-exploring-implications-of-mandatory-safety-standards-in-retail -and-foodservice/; Dec. 12, 2019; pp. 1-20.
Gaukler, Gary et al.; "Establishing Dynamic Expiration Dates for Perishables: An Application of RFID and Sensor Technology"; International Journal of Production Economics; vol. 193; Jul. 25, 2017; pp. 617-632.
GEIE/CEMA/ITP; "Deliverable D 8.3.1.3 Newsletter edited by GEIE for industrial use N°3"; http://www.frisbee-project.eu/images/result/FRISBEE_DEL_8.3.1.3.pdf; Mar. 13, 2012; pp. 1-10.
GEIE/CEMA/ITP; "Deliverable D8.3.1.2 Newsletter edited by GEIE for industrial use N°2"; http://www.frisbee-project.eu/images/result/FRISBEE_DEL_8.3.1.2.pdf; Oct. 27, 2011; pp. 1-10.
Giannakourou, M. C., et al.; "Application of a TTI-Based Distribution Management System for Quality Optimization of Frozen Vegetables at the Consumer End"; Journal of Food Science, vol. 68, Issue 1; Jan. 2003; pp. 201-209.
Hertog, M. L. A. T. M., et al.; "Shelf-life modelling for first-expired-first-out warehouse management"; Philosophical Transactions of the Royal Society; http://dx.doi.org/10.1098/rsta.2013.0306; 2014; pp. 1-15.
IBM; "DHL Breaks New Ground with RFID-Based Real-Time Tracking of Sensitive Shipments"; ftp://ftp.software.ibm.com/software/solutions/pdfs/ODC00298-USEN-00.pdf; Available as early as Mar. 2007; pp. 1-4.
Infratab; "Infratab Freshtime RF Sensor Blockchain Solutions for the Fresh Seafood Cold Chain"; https://web.aimglobal.org/external/wcpages/wcecommerce/eComItemDetailsPage.aspx?ItemID=656; 2019; pp. 1-5.
Jedermann, Reiner, et al.; "Communication techniques and challenges for wireless food quality monitoring"; Philosophical Transactions of the Royal Society; http://dx.doi.org/10.1098/rsta.2013.0304; 2014; pp. 1-18.
Jedermann, Reiner, et al.; "Reducing food losses by intelligent food logistics"; Philosophical Transactions of the Royal Society; http://dx.doi.org/10.1098/rsta.2013.0302; 2014; pp. 1-20.
Kader, A. A.; "Pre- and Postharvest Factors Affecting Fresh Produce Quality, Nutritional Value, and Implications for Human Health"; Proceedings of the International Congress of Food Production and the Quality of Life, Sassari (Italy) Sep. 4-8, 2000, vol. 1, pp. 109-119.
Ketzenberg, M., et al.; "Expiration Dates and Order Quantities for Perishables"; European Journal of Operational Research; vol. 266, Issue 2; Apr. 2018; pp. 569-584.

(56) References Cited

OTHER PUBLICATIONS

Ketzenberg, M., et al.; "Managing Perishables with Time and Temperature History"; Production and Operations Management; vol. 24, Issue 1; Jan. 2015; pp. 54-70.
Ketzenberg, M., et al.; "The Value of RFID Technology Enabled Information to Manage Perishables"; https://pdfs.semanticscholar.org/bded/16af2e689b4fdcea7f8421f6e012a6041324.pdf; Apr. 2009; pp. 1-37.
Koutsoumanis, K., et al.; "Development of a safety monitoring and assurance system for chilled food product"; International Journal of Food Microbiology, vol. 100; 2005; pp. 253-260.
Leake, Linda L.; "The Search for Shelf Life Solutions"; https://www.ift.org/news-and-publications/food-technology-magazine/issues/2007/n ovember/columns/laboratory?page=viewall: Nov. 1, 2007; pp. 1-8.
McBeath, Bill; "Winning the Freshness Wars: Creating Shopper Loyalty and Improving Profitability in Retail Grocery"; https://www.zestlabs.com/wp-content/uploads/2016/11/ZL_WP_FreshnessWars_060415.p df; Available as early as Feb. 2013; pp. 1-16.
Mehring, Peter; "Blockchain for Food Safety—Addressing the Challenges"; https://www.zestlabs.com/will-blockchain-solve-food-safety-challenges/; Sep. 26, 2018; pp. 1-4.
Mehring, Peter; "Zest Labs CEO Peter Mehring on the Walmart Lawsuit"; https://www.zestlabs.com/zest-labs-ceo-peter-mehring-walmart-lawsuit/; Aug. 1, 2018; pp. 1-4.
NBC Bay Area; "Tech Company Helps Inspect Food During Shutdown"; https://www.nbcbayarea.com/news/tech/tech-company-helps-inspect-food-during-shutdown_bay-area/4851; Jan. 11, 2019; pp. 1-6.
NRDC; "Wasted: How America is Losing up to 40 Percent of Its Food From Farm to Fork Landfill"; https://www.nrdc.org/sites/default/files/wasted-2017-report.pdf; Available as early as Aug. 2017; pp. 1-58.
Opatova, H.; "Deliverable 8.2.2.1 Organisation of a Workshop in Prague 2011 at International Congress of Refrigeration"; http://www.frisbee-project.eu/images/result/FRISBEE_DEL_8.2.2.1.pdf; Oct. 27, 2011; pp. 1-8.
Payne, Kevin; "New Verizon Ad Sheds Light on Important Food Safety Issues"; https://www.zestlabs.com/new-verizon-ad-sheds-light-on-important-food-safety-iss ues/; Dec. 15, 2017; pp. 1-4.
Payne, Kevin; "Agriculture Technology and "The Messy Middle""; https://www.zestlabs.com/agriculture-technology-messy-middle/; Jun. 25, 2019; pp. 1-4.
Payne, Kevin; "Are You Ready to Make 2018 Your Best Year Ever?" https://www.zestlabs.com/are-you-ready-to-make-2018-your-best-year-ever/; Feb. 13, 2018; pp. 1-4.
Payne, Kevin; "Blockchain for Fresh Food Supply Chains—Reality Sets In?"; https://www.zestlabs.com/blockchain-fresh-supply-chains-reality/; May 7, 2019; pp. 1-4.
Payne, Kevin; "Cold Chain Visibility: Who's Winning the Freshness Wars?"; https://www.zestlabs.com/cold-chain-visibility-freshness-wars/; Apr. 9, 2019; pp. 1-4.
Payne, Kevin; "Cold Supply Chain Variability—The Impact of Delays"; https://www.zestlabs.com/cold-supply-chain-variability/; Apr. 23, 2019; pp. 1-4.
Payne, Kevin; "Earth Day 2019 and Looking Ahead to 2020"; https://www.zestlabs.com/earth-day-2019/; Apr. 30, 2019; pp. 1-4.
Payne, Kevin; "Finding the Right Tools: Can Blockchain and IOT Fix the Fresh Food Supply Chain?—Register for the Webinar"; https://www.zestlabs.com/finding-the-right-tools-can-blockchain-and-iot-fix-the- fresh-food-supply-chain-register-for-the-webinar/; Feb. 27, 2018; pp. 1-4.
Payne, Kevin; "Food Grower And Supplier Challenges: The Top 10"; https://www.zestlabs.com/food-growers-suppliers-challenges/; Feb. 19, 2019; pp. 1-4.
Payne, Kevin; "Food Labels and Food Waste—A Solution"; https://www.zestlabs.com/food-labels-food-waste/; Mar. 12, 2019; pp. 1-4.
Payne, Kevin; "Food Safety Tips: Three Things to Consider"; https://www.zestlabs.com/food-safety-tips-three-things-to-consider/; Jul. 2, 2019; pp. 1-4.
Payne, Kevin; "Fresh Produce and Health: What's the Connection?"; https://www.zestlabs.com/fresh-produce-health-interrelationship/; Apr. 2, 2019; pp. 1-4.
Payne, Kevin; "Grocery Shopper Trends 2019: Key Insights"; https://www.zestlabs.com/grocery-shopper-trends-2019-key-insights/; Jul. 23, 2019; pp. 1-4.
Payne, Kevin; "How to Feed a Hungry Planet: Food for Thought"; https://www.zestlabs.com/feed-a-hungry-planet/; Aug. 6, 2019; pp. 1-4.
Payne, Kevin; "Hyped Up? Blockchain and Why a Hybrid Model is Best"; https://www.zestlabs.com/hyped-up-blockchain-the-fresh-food-supply-chain-and-why -a-hybrid-model-is-best/; Jan. 30, 2018; pp. 1-4.
Payne, Kevin; "I'll Never Look at Strawberries the Same Way"; https://www.zestlabs.com/ill-never-look-at-strawberries-the-same-way/; Dec. 15, 2017; pp. 1-4.
Payne, Kevin; "Improving Operational Efficiency: TQM for the Fresh Food Supply Chain"; https://www.zestlabs.com/improving-operational-efficiency-deming-drucker/; Aug. 27, 2019; pp. 1-4.
Payne, Kevin; "Increasing Trucking Costs Further Squeezes Grocery Margins—Don't Waste Your Money!" https://www.zestlabs.com/increasing-trucking-costs-further-squeezes-grocery-marg ins-dont-waste-your-money/; Feb. 6, 2018; pp. 1-4.
Payne, Kevin; "IoT Sensors and Reducing Food Waste"; https://www.zestlabs.com/iot-sensors-reduce-food-waste/; Feb. 12, 2019; pp. 1-4.
Payne, Kevin; "Millennials Want True Transperency"; https://www.zestlabs.com/millennials-want-true-transparency/; Jan. 9, 2018; pp. 1-4.
Payne, Kevin; "Myth Busting: Produce Shrink is Caused at the Store"; https://www.zestlabs.com/myth-busting-produce-shrink-occurs-at-the-store/; Feb. 20, 2018; pp. 1-4.
Payne, Kevin; "New Zest Fresh for Produce Modules: Rapid Implementations and Faster ROI"; https://www.zestlabs.com/zest-fresh-produce-modules/; Jul. 10, 2019; pp. 1-4.
Payne, Kevin; "Online Grocery Shopping Options Abound But . . . "; https://www.zestlabs.com/online-grocery-shopping/; Feb. 5, 2019; pp. 1-4.
Payne, Kevin; "Preventing Food Waste: Multiple Approaches"; https://www.zestlabs.com/preventing-food-waste-multiple-approaches/; Jul. 16, 2019; pp. 1-4.
Payne, Kevin; "Proactive Food Safety: Moving the Industry Forward"; https://www.zestlabs.com/proactive-food-safety/; Aug. 13, 2019; pp. 1-4.
Payne, Kevin; "Produce Marketing: Brandstorm Offers A Wealth Of Insights"; https://www.zestlabs.com/produce-marketing-ideas; Feb. 26, 2019; pp. 1-4.
Payne, Kevin; "Reducing Fresh Food Waste: Addressing the Problem"; https://www.zestlabs.com/reducing-fresh-food-waste-problem/; Mar. 5, 2019; pp. 1-4.
Payne, Kevin; "Rethinking Food Safety and the Supply Chain"; https://www.zestlabs.com/rethinking-food-safety-supply-chain/; May 14, 2019; pp. 1-5.
Payne, Kevin; "Salad Kits: How to Ensure Freshness"; https://www.zestlabs.com/salad-kits-fresh/; Apr. 16, 2019; pp. 1-4.
Payne, Kevin; "Shelf-life Variability at Grocery Stores: Half-bad is Not Good"; https://www.zestlabs.com/shelf-life-variability-among-leading-grocery-stores/; Jun. 10, 2019; pp. 1-4.
Payne, Kevin; "Start the Year Fresh!" https://www.zestlabs.com/start-the-year-fresh/; Jan. 16, 2018; pp. 1-4.
Payne, Kevin; "Supply Chain Waste: Can We Fix the Problem? (Yes)"; https://www.zestlabs.com/supply-chain-waste/; Jul. 30, 2019; pp. 1-5.
Payne, Kevin; "Sustainability and the Supply Chain"; https://www.zestlabs.com/sustainability-supply-chain/; Jun. 18, 2019; pp. 1-4.
Payne, Kevin; "Sustainability or Greenwashing" https://www.zestlabs.com/sustainability-or-greenwashing/; Jan. 23, 2018; pp. 1-4.
Payne, Kevin; "The "Best If Used By" Date Label: Will It Reduce Food Waste?"; https://www.zestlabs.com/best-if-used-by-date-label/; Jun. 4, 2019; pp. 1-4.

(56) References Cited

OTHER PUBLICATIONS

Payne, Kevin; "The Emergence of Brand Marketing in Produce"; https://www.zestlabs.com/brand-marketing-produce/; Aug. 20, 2019; pp. 1-4.
Payne, Kevin; "The Grocery Shopping Experience: Fresh Foods, Fresh Ideas"; https://www.zestlabs.com/grocery-shopping-experience-fresh-foods/; May 21, 2019; pp. 1-4.
Payne, Kevin; "To Use or Not to Use—What's Up With Date Labels" https://www.zestlabs.com/date-label/; Jan. 2, 2018; pp. 1-4.
Payne, Kevin; "Want to Improve Your Grocery Margins? Take a Look at Your Supply Chain"; https://www.zestlabs.com/want-to-improve-your-grocery-margins-take-a-look-at-you r-supply-chain/; Dec. 19, 2017; pp. 1-4.
Payne, Kevin; "World Hunger Day 2019: Sustainability"; https://www.zestlabs.com/world-hunger-day-2019-sustainability/; May 28, 2019; pp. 1-4.
Payne, Kevin; "Your Technology Roadmap for Digital Transformation"; https://www.zestlabs.com/technology-roadmap/; Mar. 26, 2019; pp. 1-4.
Payne, Kevin; "A Picture Is Worth . . . "; https://www.zestlabs.com/a-picture-is-worth/; Apr. 3, 2018; pp. 1-4.
Payne, Kevin; "Before and After—The Benefits of Digital Transformation"; https://www.zestlabs.com/benefits-digital-transformation/; Jan. 29, 2019; pp. 1-5.
Payne, Kevin; "Being Proactive: What We Can Learn from Football"; https://www.zestlabs.com/being-proactive-learn-from-football/; Jul. 17, 2018; pp. 1-4.
Payne, Kevin; "Digital Transformation Technology: Is It Finally Time?"; https://www.zestlabs.com/digital-transformation-technology/; Aug. 7, 2018; pp. 1-4.
Payne, Kevin; "Experience the Many Benefits of Family Meals"; https://www.zestlabs.com/benefits-family-meals/; Sep. 3, 2019; pp. 1-4.
Payne, Kevin; "First Principles Thinking and the Fresh Food Supply Chain"; https://www.zestlabs.com/first-principles-thinking/; Oct. 2, 2018; pp. 1-4.
Payne, Kevin; "Five Days? The Causes of Shelf-life Variability"; https://www.zestlabs.com/five-days-shelf-life-variability/; Nov. 20, 2018; pp. 1-4.
Payne, Kevin; "Food Service Delivery: This Isn't What I Ordered!"; https://www.zestlabs.com/isnt-what-ordered/; Aug. 28, 2018; pp. 1-4.
Payne, Kevin; "Food Spoilage: The Impact On Your Business"; https://www.zestlabs.com/food-spoilage-impact-business/; Jan. 15, 2019; pp. 1-4.
Payne, Kevin; "Food Sustainability Goals: Noble But Are They Viable?"; https://www.zestlabs.com/food-sustainability-goals/; Aug. 14, 2018; pp. 1-4.
Payne, Kevin; "Fresh Food Industry Trends 2019—Our Predictions"; https://www.zestlabs.com/fresh-food-industry-trends-2019/; Jan. 2, 2019; pp. 1-4.
Payne, Kevin; "Fresh Food Industry Trends from 2018"; https://www.zestlabs.com/fresh-food-industry-trends-2018/; Dec. 11, 2018; pp. 1-4.
Payne, Kevin; "Fresh Food Sustainability—It's More Than Field to Fork"; https://www.zestlabs.com/fresh-food-sustainability/; Jan. 22, 2019; pp. 1-4.
Payne, Kevin; "Freshness Capacity: Strawberries Are Like Your Cell Phone . . . "; https://www.zestlabs.com/your-fresh-strawberries-are-like-your-cellphone/; Jul. 10, 2018; pp. 1-4.
Payne, Kevin; "Grocers Are Applying Artificial Intelligence"; https://www.zestlabs.com/grocers-turning-artificial-intelligence/; Oct. 9, 2018; pp. 1-4.
Payne, Kevin; "Growers And Suppliers—What Really Happens In The Food Supply Chain"; https://www.zestlabs.com/what-happens-fresh-food-supply-chain/; Apr. 24, 2018; pp. 1-5.
Payne, Kevin; "Improving Post-Harvest Operational Efficiency"; https://www.zestlabs.com/improving-operational-efficiency/; Sep. 18, 2018; pp. 1-4.
Payne, Kevin; "Is Your Fresh Food Supply Chain Stuck In The '60s?"; https://www.zestlabs.com/is-your-fresh-food-supply-chain-stuck-in-the-60s/; Mar. 13, 2018; pp. 1-4.
Payne, Kevin; "It's (Past) Time for Freshness Management"; https://www.zestlabs.com/managing-fresh-food-shelf-life/; Nov. 27, 2018; pp. 1-4.
Payne, Kevin; "It's Like Waze For The Fresh Food Supply Chain"; https://www.zestlabs.com/waze-fresh-food-supply-chain/; Apr. 10, 2018; pp. 1-5.
Payne, Kevin; "Let's Celebrate National Salad Month!"; https://www.zestlabs.com/lets-celebrate-national-salad-month/; May 1, 2018; pp. 1-4.
Payne, Kevin; "Let's Start At The Beginning"; https://www.zestlabs.com/lets-start-at-the-beginning/; May 15, 2018; pp. 1-4.
Payne, Kevin; "Margins Matter—Don't Get Squeezed"; https://www.zestlabs.com/6931-2/; Apr. 17, 2018; pp. 1-4.
Payne, Kevin; "Perishable Food Waste Cuts Profits & Raises Greenhouse Gases"; https://www.zestlabs.com/food-waste-profits-greenhouse-gases/; Sep. 11, 2018; pp. 1-4.
Payne, Kevin; "PMA Fresh Summit 2018—Wow!"; https://www.zestlabs.com/pma-fresh-summit/; Oct. 23, 2018; pp. 1-4.
Payne, Kevin; "PMA's Fresh Summit: Eat Up!"; https://www.zestlabs.com/pma-fresh-summit-2018/; Oct. 16, 2018; pp. 1-4.
Payne, Kevin; "Poor Quality Produce: Never Going Back Again"; https://www.zestlabs.com/never-going-back-again/; Jul. 3, 2018; pp. 1-4.
Payne, Kevin; "Premature Food Spoilage: Uh Oh, It's the Fuzz!"; https://www.zestlabs.com/uh-oh-its-the-fuzz/; Jun. 19, 2018; pp. 1-4.
Payne, Kevin; "Produce Shelf Life Extenders and Fresh Food Waste"; https://www.zestlabs.com/shelf-life-extenders-food-waste/; Nov. 13, 2018; pp. 1-4.
Payne, Kevin; "Refed: Committed to Reducing U.S. Food Waste"; https://www.zestlabs.com/refed-committed-reducing-waste/; Oct. 30, 2018; pp. 1-4.
Payne, Kevin; "Romaine Lettuce Labeling—Zest Fresh Can Help"; https://www.zestlabs.com/romaine-lettuce-labeling/; Dec. 4, 2018; pp. 1-4.
Payne, Kevin; "Saving Money Day 1—Invest $1, Get $9 Back";https://www.zestlabs.com/saving-money-day-1/; Nov. 6, 2018; pp. 1-4.
Payne, Kevin; "September Is National Family Meals Month"; https://www.zestlabs.com/september-family-meals-month/; Sep. 4, 2018; pp. 1-4.
Payne, Kevin; "Shelf-life Variability in Produce: The Five Causes"; https://www.zestlabs.com/shelf-life-variability-produce-five-causes/; Jan. 8, 2019; pp. 1-4.
Payne, Kevin; "Solving the Problem of Fresh Produce Waste"; https://www.zestlabs.com/solving-problem-fresh-food-waste/; Dec. 18, 2018; pp. 1-4.
Payne, Kevin; "Stay Cool! (And Visit Us at United Fresh!)"; https://www.zestlabs.com/stay-cool-and-visit-us-at-united-fresh/; Jun. 5, 2018; pp. 1-4.
Payne, Kevin; "Stop Doing That!"; https://www.zestlabs.com/stop-doing-that/; May 29, 2018; pp. 1-4.
Payne, Kevin; "Supply Chain Performance: The Fox and the Henhouse"; https://www.zestlabs.com/fox-hen-house/; Jun. 26, 2018; pp. 1-4.
Payne, Kevin; "The Fresh Food Industry and Charles Darwin"; https://www.zestlabs.com/charles-darwin-fresh-food-industry/; Aug. 21, 2018; pp. 1-4.
Payne, Kevin; "The Game of (Shelf) Life"; https://www.zestlabs.com/game-shelf-life/; Sep. 25, 2018; pp. 1-4.
Payne, Kevin; "Timing Is Everything—The Impact Of Cut-To-Cool Time On Freshness"; https://www.zestlabs.com/timing-is-everything-the-impact-of-cut-to-cool-time-on- freshness/; May 8, 2018; pp. 1-5.
Payne, Kevin; "What to do to Build Grocery Store Loyalty?"; https://www.zestlabs.com/grocery-store-loyalty/; Jul. 24, 2018; pp. 1-4.
Payne, Kevin; "What? No Bacon? (Cue Ominous Music)"; https://www.zestlabs.com/what-no-bacon-cue-ominous-music/; Mar. 6, 2018; pp. 1-5.

(56) References Cited

OTHER PUBLICATIONS

Payne, Kevin; "What's In The Bag?"; https://www.zestlabs.com/whats-in-the-bag/; May 22, 2018; pp. 1-4.
Payne, Kevin; "Where's The Beef (Been)?"; https://www.zestlabs.com/wheres-the-beef-been/; Mar. 27, 2018; pp. 1-5.
Payne, Kevin; "Zest Labs Offers Fresh Wishes for the New Year"; https://www.zestlabs.com/zest-labs-fresh-wishes-new-year/; Dec. 24, 2018; pp. 1-4.
ReFED; "A Roadmap to Reduce U.S. Food Waste by 20 Percent"; https://www.refed.com/downloads/ReFED_Report_2016.pdf; 2016; pp. 1-96.
ReFED; "Restaurant Food Waste Action Guide"; https://www.refed.com/downloads/Restaurant_Guide_Web.pdf; 2018; pp. 1-44.
Ruiz-Garcia, Luis et al.; "Monitoring Cold Chain Logistics by Means of RFID"; http://cdn.intechweb.org/pdfs/8493.pdf; Feb. 1, 2010; pp. 1-16.
Ryan, John; "Why Blockchain Will Be Used to Improve Distribution Food Safety, Quality, and Traceability"; https://www.foodsafetymagazine.com/enewsletter/why-blockchain-will-be-used-to-improve-distribution-food-safety-quality-and-traceability/; Feb. 5, 2019; pp. 1-3.
Scalco, Dan; "5 Ways to Ensure Meals Stay Fresh and Safe in Transit"; https://www.zestlabs.com/meals-stay-fresh-safe-transit/; Jun. 12, 2018; pp. 1-4.
Scotto Di Tella, F.; "Deliverable D8.3.1.1 Newsletter edited by GEIE for industrial use N°1"; http://www.frisbee-project.eu/images/result/FRISBEE_DEL_8.3.1.1.pdf; May 6, 2011; pp. 1-9.
Shacklett, Mary; "Customer Retention and Growth in Today's Competitive Retail Grocery Environment"; https://www.zestlabs.com/downloads/Food-Freshness-and-Customer-Satisfaction-Transworld-Research-April-2019.pdf; Apr. 2019; pp. 1-7.
Shacklett, Mary; "Improving Profits and Operational Efficiency on the Farm"; https://www.zestlabs.com/downloads/Improving-Operational-Efficiency-on-the-Farm-Transworld-Research-2018.pdf; Available as early as 2018; pp. 1-6.
Shacklett, Mary; "Optimizing Profit Margins in a Changing Retail Grocery Industry"; https://www.zestlabs.com/downloads/Optimizing-Profit-Margins-Transworld.pdf; 2018; pp. 1-10.
Siawsolit, Chokdee et al.; "The Value of Demand Information in Omni-Channel Grocery Retailing"; https://www.researchgate.net/publication/331048136_The_Value_of_Demand_Information_in_Omni-Channel_Grocery_Retailing; Available as early as Jan. 2019; pp. 1-11.
Stahl, Valerie et al.; "Deliverable D.3.2.4.2 Literature review and experimental data of chilled and frozen meat quality and safety models"; http://www.frisbee-project.eu/images/result/FRISBEE_DEL_3.2.4.2.pdf; Jun. 6, 2011; pp. 1-28.
Sunny George, Gwanpua; "Deliverable D3.2.4.1 Literature review and experimental data of chilled apple quality models"; http://www.frisbee-project.eu/images/result/FRISBEE_DEL_3.2.4.1.pdf; Mar. 1, 2011; pp. 1-24.
Swedberg, Claire; "DOD Considers RFID-based Solutions for Tracking Food's Shelf Life"; https://www.rfidjournal.com/articles/pdf?11423; Feb. 11, 2014; pp. 1-3.
Swedberg, Claire; "Researchers Seek to Reduce Wastage for First-Strike Rations"; https://www.rfidjournal.com/articles/pdf?9162; Jan. 26, 2012; pp. 1-4.
Swedberg, Claire; "Schuitema Ponders Future of Fresh-Chain Pilot"; https://www.rfidjournal.com/articles/pdf?3793; Dec. 10, 2007; pp. 1-4.
Swedberg, Claire; "Starbucks Keeps Fresh with RFID"; https://www.rfidjournal.com/articles/view?2890; Dec. 13, 2006; pp. 1-1.
Taoukis, P. S., et al.; "Applicability of Time—Temperature Indicators as Shelf Life Monitors of Food Products"; Journal of Food Science; vol. 54, Issue 4; Jul. 1989; pp. 783-788.
Taoukis, P. S., et al.; "Use of time-temperature integrators and predictive modelling for shelf life control of chilled fish under dynamic storage conditions"; International Journal of Food Microbiology, vol. 53; 1999; pp. 21-31.
Taoukis, Petros et al.; "Deliverable D.2.1.2 Temperature monitoring techniques and traceability systems along the cold chain";http://www.frisbee-project.eu/images/result/FRISBEE_DEL_2%201%202.pdf; Jul. 26, 2011; pp. 1-28.
Taoukis, Petros; "Deliverable D 3.2.4.4 Literature review and experimental data of frozen milk products and vegetables quality models"; http://www.frisbee-project.eu/images/result/FRISBEE_DEL_3-2-4-4.pdf; Jun. 6, 2011; pp. 1-24.
This New World By Huffpost; "Eating Ugly: The Food Waste That Could Refeed America"; https://www.facebook.com/ThisNewWorldHuffPost/videos/428476821288487; Apr. 22, 2019; pp. 1-9.
Trust in Food™; "Sustainability Research Report 2019"; https://www.zestlabs.com/downloads/Trust-In-Food-Sustainability-Survey-2019.pdf; Available as early as Jul. 18, 2019; pp. 1-19.
Wells, John H., et al.; "A Kinetic Approach to Food Quality Prediction using Full-History Time-Temperature Indicators"; Journal of Food Science; vol. 53, Issue 6; Nov. 1988; pp. 1866-1871.
Wells, John H., et al.; "A Quality-Based Inventory Issue Policy For Perishable Foods"; Journal of Food Processing & Preservation; vol. 12, Issue 4; Jan. 1989; pp. 271-292.
Wells, John Henry, et al.; "Application of Time-Temperature Indicators in Monitoring Changes in Quality Attributes of Perishable and Semiperishable Foods"; Journal of Food Science; vol. 53, Issue 1; Jan. 1988; pp. 148-152, 156.
Weston, L.A. et al.; "Preharvest Factors Affecting Postharvest Quality of Vegetables"; HortScience; vol. 32(5), Aug. 1997, pp. 812-816.
Williamson, Katie et al.; "Climate Change Needs Behavior Change"; https://www.zestlabs.com/downloads/2018-CCNBC-Report.pdf; 2018; pp. 1-22.
Zelem, MC.; "Deliverable D.2.3.1 National legal and ethical requirements for the surveys"; http://www.frisbee-project.eu/images/result/FRISBEE_DEL_2.3.1.pdf; Jun. 23, 2011; pp. 1-68.
*Zest Labs, Inc.* v *Walmart*; Bohling, Joshua; "Transcript of the Testimony of Bohling, Joshua"; Bushman Court Reporting; Case No. 4:18-CV-00500-JM; Aug. 15-16, 2019; pp. 5-6, 47-48, 52-69, 78, 80-82, 85, 87, 98-102, 107-134, 137-145, 158-163, 182-184, 209-210, 233-234, 239-242, 246, and 357.
*Zest Labs, Inc.* v *Walmart*; Dickinson, Q. Todd; "Expert Report of Q. Todd Dickinson"; United States District Court for the Eastern District of Arkansas; Case No. 4:18-CV-00500-JM; Oct. 29, 2019; pp. 1-33.
*Zest Labs, Inc.* v *Walmart*; Kunin, Stephen G.; "Rebuttal Expert Report of Stephen G. Kunin"; United States District Court for the Eastern District of Arkansas; Case No. 4:18-CV-00500-JM; Nov. 25, 2019; pp. 1-38.
*Zest Labs, Inc.* v *Walmart*; Zest Labs, Inc. et al.; "COMPLAINT"; United States District Court for the Eastern District of Arkansas; Case No. 4:18-CV-00500-JM; Aug. 1, 2018; pp. 1-26.
Zest Labs; "Blockchain for Supply Chains"; https://www.zestlabs.com/challenges/blockchain-for-supply-chains/; Available as early as Jul. 18, 2019; pp. 1-4.
Zest Labs; "Food Safety and the Supply Chain"; https://www.zestlabs.com/challenges/food-safety/; Available as early as Jul. 18, 2019; pp. 1-5.
Zest Labs; "Food Supplier Operational Efficiency"; https://www.zestlabs.com/challenges/food-supplier-operational-efficiency/; Available as early as Jul. 18, 2019; pp. 1-5.
Zest Labs; "Food Waste is a Significant Problem"; https://www.zestlabs.com/challenges/food-waste-challenge/; Available as early as Jul. 18, 2019; pp. 1-6.
Zest Labs; "Fresh Food Supply Chain"; https://www.zestlabs.com/challenges/fresh-food-supply-chain/; Available as early as Jul. 18, 2019; pp. 1-5.
Zest Labs; "Fresh Food Sustainability"; https://www.zestlabs.com/challenges/fresh-food-sustainability/; Available as early as Jul. 18, 2019; pp. 1-4.
Zest Labs; "Fresh Produce"; http://www.zestlabs.com/fresh-produce; Available as early as Oct. 21, 2017; pp. 1-14.
Zest Labs; "On-Demand Delivery"; https://www.zestlabs.com/on-demand-delivery/; Available as early as Oct. 22, 2017; pp. 1-7.

(56) References Cited

OTHER PUBLICATIONS

Zest Labs; "Post-Harvest Technology"; https://www.zestlabs.com/challenges/post-harvest-technology/; Available as early as Jul. 18, 2019; pp. 1-8.
Zest Labs; "The Freshest Produce"; https://www.zestlabs.com/resources; Available as early as May 2, 2018; pp. 1-16.
Zest Labs; "Zest Fresh—Deep Dive"; https://www.zestlabs.com/resources; Available as early as May 2, 2018; pp. 1-15.
Zest Labs; "Zest Fresh Differentiation"; https://www.zestlabs.com/zest-fresh-differentiation/; Available as early as Jul. 18, 2019; pp. 1-6.
Zest Labs; "Zest Fresh for Beef, Poultry, Pork and Seafood"; https://www.zestlabs.com/zest-fresh-for-protein/; Available as early as Jul. 18, 2019; pp. 1-5.
Zest Labs; "Zest Fresh for Grocers"; https://www.zestlabs.com/zest-fresh-for-produce-for-grocers/; Available as early as Jul. 18, 2019; pp. 1-13.
Zest Labs; "Zest Fresh for Growers, Packers, and Shippers"; https://www.zestlabs.com/zest-fresh-for-growers-and-suppliers/; Available as early as Jul. 18, 2019; pp. 1-17.
Zest Labs; "Zest Fresh for Restaurants"; https://www.zestlabs.com/zest-fresh-for-produce-for-restaurants/; Available as early as Jul. 18, 2019; pp. 1-13.
Zest Labs; "Zest Fresh Grower Testimonial"; https://www.zestlabs.com/resources; Available as early as May 2, 2018; pp. 1-13.
Zest Labs; "Zest Fresh Overview"; https://www.zestlabs.com/resources; Available as early as May 2, 2018; pp. 1-19.
Zest Labs; "Zest Fresh Use Cases"; https://www.zestlabs.com/zest-fresh-use-cases/; Available as early as Jul. 18, 2019; pp. 1-6.
Zest Labs; "Zest Fresh: Pallet-level Quality Management from Harvest to Store"; http://www.zestlabs.com/zest-fresh; Available as early as Oct. 29, 2017; pp. 1-10.
Zest Labs; "Zest Labs Overview"; https://www.zestlabs.com/resources; Available as early as Aug. 1, 2018; pp. 1-13.
Zest Labs; ". . . Not Worth a Thousand Words—Why Traditional Temperature Loggers and Imaging Technologies are Inadequate to Determine Freshness and Reduce Waste"; https://www.zestlabs.com/wp-content/uploads/2018/03/WP-05-0318-Not-Worth-A-Thous and-Words.pdf; Mar. 5, 2018; pp. 1-6.
Zest Labs; "10 Limitations of Traditional Temperature Data Loggers And Why They're No Longer Adequate for the Cold Chain"; https://www.zestlabs.com/wp-content/uploads/2018/05/PB-04-0418-10-Limitations-of-Data-Loggers.pdf; May 4, 2018; pp. 1-3.
Zest Labs; "Before and After—The Benefits of Digital Transformation in the Fresh Food Supply Chain"; https://www.zestlabs.com/downloads/Before-and-After-Digital-Transformation.pdf; Jan. 13, 2019; pp. 1-6.
Zest Labs; "Blockchain and Achieving True Transparency—Proactively Managing Food Safety and Freshness with Blockchain and IoT Technologies"; https://www.zestlabs.com/wp-content/uploads/2018/01/WP-08-0118.Blockchain.and_.Achieving.True_.Transparency-1.pdf; Jan. 8, 2018; pp. 1-4.
Zest Labs; "Blockchain and Its Value to Suppliers"; https://www.zestlabs.com/downloads/Blockchain-and-Its-Value-to-Suppliers.pdf; Available as early as Jul. 18, 2019; pp. 1-5.
Zest Labs; "Comparing Pallet- and Trailer-level Temperature Monitoring—Implications on Quality, Freshness, Traceability and Profitability for Retail Grocers"; https://www.zestlabs.com/wp-content/uploads/2018/03/WP-04-0318-Pallet-vs-Trailer .pdf; Mar. 4, 2018; pp. 1-4.
Zest Labs; "Freshness Baseline Study—Sample Report"; http://www.zestlabs.com/wp-content/uploads/2018/03/Zest-Labs-Sample-Baseline-Rep ort.pdf; Available as early as Mar. 2018; pp. 1-11.
Zest Labs; "Freshness Myths—False Beliefs That Lead to Food Waste"; https://www.zestlabs.com/downloads/Freshness-Myths.pdf; Aug. 7, 2018; pp. 1-5.
Zest Labs; "Half-bad Is Not Good"; https://www.zestlabs.com/downloads/Grocery-Store-Variability.pdf; Jun. 15, 2019; pp. 1-11.

Zest Labs; "Improve Operational Efficiency—Optimize Labor and Process Adherence to Reduce Costs"; https://www.zestlabs.com/downloads/Improving-Operational-Efficiency.pdf; Available as early as Jul. 18, 2019; pp. 1-3.
Zest Labs; "Improving Quality and Profitability for Retail Grocers—The Benefits of Pallet-level Monitoring for the Fresh and Perishable Food Cold Chain"; https://www.zestlabs.com/wp-content/uploads/2017/12/WP-01-1117.Improving.Quality .and_.Profitability.for_.Retail.Grocers.pdf; Nov. 1, 2017; pp. 1-8.
Zest Labs; "Let's Start at the Beginning—Reducing Shrink Begins at Harvest"; https://www.zestlabs.com/wp-content/uploads/2018/05/WP-12-0518-Lets-Start-at-the -Beginning.pdf; May 12, 2018; pp. 1-4.
Zest Labs; "Margins Matter—Reducing Fresh Food Waste to Improve Product Margins by 6% or More"; https://www.zestlabs.com/wp-content/uploads/2018/04/WP-11-0418-Margins-Matter-1. pdf; Apr. 11, 2018; pp. 1-6.
Zest Labs; "Measuring and Managing Operational Efficiency for Growers and Suppliers"; https://www.zestlabs.com/downloads/Zest-Fresh-Metrics-Datasheet.pdf; Aug. 25, 2019; pp. 1-5.
Zest Labs; "Monitoring the Safety and Quality of Fresh, Frozen and Processed Foods"; https://www.zestlabs.com/wp-content/uploads/2016/03/IN-SB-FreshProduce_RestaurantFoodService_031016.pdf; Mar. 10, 2016; pp. 1-2.
Zest Labs; "Pallet-level Quality Management from Harvest to Store"; https://www.zestlabs.com/wp-content/uploads/2016/03/IN_SB_Foodindustry_ProduceGr owers_031016.pdf; Mar. 10, 2016; pp. 1-2.
Zest Labs; "Poor Customer Experiences—Half-Bad is Not Good! A Shelf-Life Variability Study"; https://www.zestlabs.com/downloads/Variability-Infographic.pdf; Available as early as Jul. 2019; pp. 1-1.
Zest Labs; "Proactive Freshness Management: Modernizing the Fresh Food Supply Chain to Reduce Waste and Improve Profitability"; https://www.zestlabs.com/downloads/Proactive-Freshness-Management.pdf; Feb. 6, 2019; pp. 1-7.
Zest Labs; "Reduce Shrink, Improve Profitability and Quality for Fresh Food"; https://www.zestlabs.com/wp-content/uploads/2016/03/IN-SB-FreshProduce_RetailGro cers_031016.pdf; Mar. 10, 2016; pp. 1-3.
Zest Labs; "Shelf-life Variability Begins in the Field—Produce Pallets Harvested on the Same Day Vary by as Much as 86 Percent, Contributing to Shrink and Lost Profits"; https://www.zestlabs.com/wp-content/uploads/2018/02/WP-10-0218-Shelf-life-Variab ility.pdf; Feb. 10, 2018; pp. 1-4.
Zest Labs; "Strawberries—Shelf-Life Variability"; https://www.zestlabs.com/downloads/Zest-Fresh-Strawberries-Report.pdf; Available as early as Jul. 2019; pp. 1-2.
Zest Labs; "The Best of Zest 2018—A Collection of Our Most Popular Blogs"; https://www.zestlabs.com/downloads/The-Best-of-Zest-2018.pdf; Available as early as 2018; pp. 1-15.
Zest Labs; "The ZIPR Code Freshness Metric—Dynamically providing the current freshness of each pallet to help you intelligently manage product and reduce shrink throughout the fresh food supply chain"; https://www.zestlabs.com/downloads/The-ZIPR-Code.pdf; Jun. 1, 2018; pp. 1-3.
Zest Labs; "Today, You Saved $67,571—How Zest Fresh for Managing the Produce Cold Chain Reduces Waste and Saves Retailers Money . . . Beginning on Day One"; https://www.zestlabs.com/downloads/Today-You-Saved.pdf; Jun. 3, 2018; pp. 1-6.
Zest Labs; "True Transparency for Freshness Management, Food Safety, Authenticity and Traceability"; https://www.zestlabs.com/wp-content/uploads/2018/03/SO-04-0218-Zest-Fresh-for-Protein-Solution-Overview.pdf; Feb. 4, 2018; pp. 1-2.
Zest Labs; "Zest Labs FAQ and Reference Guide"; https://www.zestlabs.com/downloads/Zest-Labs-FAQ-and-Reference-Guide.pdf; Jul. 1, 2018; pp. 1-6.
Zest Labs; "Zest Labs Professional Services"; https://www.zestlabs.com/wp-content/uploads/2018/03/SO-05-0318-Zest-Labs-Profess ional-Services.pdf; Mar. 5, 2018; pp. 1-2.
*Zest Labs, Inc.* v *Walmart*; ECF No. 002; Zest Labs, Inc. et al.; "Motion for Leave To File Complaint Under Seal and To Establish Briefing Schedule Relating To Potentially Confidential Information

(56) References Cited

OTHER PUBLICATIONS in Complaint"; United States District Court for the Eastern District of Arkansas; Case No. 4:18-CV-00500-JM; Aug. 1, 2018; pp. 1-4.
*Zest Labs, Inc.* v *Walmart*; ECF No. 003; Zest Labs, Inc. et al.; "Brief in Support of Motion for Leave To File Complaint Under Seal and To Establish Briefing Schedule Relating To Potentially Confidential Information Complaint"; United States District Court for the Eastern District of Arkansas; Case No. 4:18-CV-00500-JM; Aug. 1, 2018; pp. 1-4.
*Zest Labs, Inc.* v *Walmart*; ECF No. 035; Walmart; "Defendant's Response To Plaintiffs' Motion for Leave To File Complaint Under Seal"; United States District Court for the Eastern District of Arkansas; Case No. 4:18-CV-00500-JM; Aug. 27, 2018; pp. 1-3.
*Zest Labs, Inc.* v *Walmart*; ECF No. 038; Zest Labs, Inc. et al.; "Plaintiffs' Reply in Support of Plaintiffs' Motion for Leave To File Complaint Under Seal"; United States District Court for the Eastern District of Arkansas; Case No. 4:18-CV-00500-JM; Aug. 31, 2018; pp. 1-3.
*Zest Labs, Inc.* v *Walmart*; ECF No. 041; Walmart; "Defendant's Motion for Leave To File Under Seal"; United States District Court for the Eastern District of Arkansas; Case No. 4:18-CV-00500-JM; Sep. 4, 2018; pp. 1-3.
*Zest Labs, Inc.* v *Walmart*; ECF No. 098; Walmart; "Defendant's Brief in Support of Its Motion for Protective Order and To Compel Identification of Alleged Trade Secrets"; United States District Court for the Eastern District of Arkansas; Case No. 4:18-CV-00500-JM; Feb. 11, 2019; pp. 1-29.
*Zest Labs, Inc.* v *Walmart*; ECF No. 101-01; Sammi, P. Anthony; "Exhibit A"; United States District Court for the Eastern District of Arkansas; Case No. 4:18-CV-00500-JM; Feb. 15, 2019; pp. 1-3.
*Zest Labs, Inc.* v *Walmart*; ECF No. 101-02; Tulin, Edward L.; "Exhibit B"; United States District Court for the Eastern District of Arkansas; Case No. 4:18-CV-00500-JM; Feb. 15, 2019; pp. 1-4.
*Zest Labs, Inc.* v *Walmart*; ECF No. 101-03; Tulin, Edward L.; "Exhibit C"; United States District Court for the Eastern District of Arkansas; Case No. 4:18-CV-00500-JM; Feb. 15, 2019; pp. 1-5.
*Zest Labs, Inc.* v *Walmart*; ECF No. 101-04; Zest Labs, Inc. et al.; "Exhibit D Filed Under Seal Pursuant To Order Dated Sep. 7, 2018"; United States District Court for the Eastern District of Arkansas; Case No. 4:18-CV-00500-JM; Feb. 15, 2019; 1 page.
*Zest Labs, Inc.* v *Walmart*; ECF No. 101-05; Zest Labs, Inc. et al.; "Exhibit E Filed Under Seal Pursuant To Order Dated Sep. 7, 2018"; United States District Court for the Eastern District of Arkansas; Case No. 4:18-CV-00500-JM; Feb. 15, 2019; 1 page.
*Zest Labs, Inc.* v *Walmart*; ECF No. 101; Zest Labs, Inc. et al.; "Plaintiffs' Brief in Opposition To Defendant's Motion for Protective Order and To Compel Identification of Trade Secrets"; United States District Court for the Eastern District of Arkansas; Case No. 4:18-CV-00500-JM; Feb. 15, 2019; pp. 1-28.
*Zest Labs, Inc.* v *Walmart*; ECF No. 102-01; Zest Labs, Inc. et al.; "Exhibit A"; United States District Court for the Eastern District of Arkansas; Case No. 4:18-CV-00500-JM; Feb. 20, 2019; pp. 1-28.
*Zest Labs, Inc.* v *Walmart*; ECF No. 102-02; Walmart; "Exhibit B"; United States District Court for the Eastern District of Arkansas; Case No. 4:18-CV-00500-JM; Feb. 20, 2019; pp. 1-59.
*Zest Labs, Inc.* v *Walmart*; ECF No. 102-03; Zest Labs, Inc. et al.; "Exhibit C Filed Under Seal"; United States District Court for the Eastern District of Arkansas; Case No. 4:18-CV-00500-JM; Feb. 20, 2019; 1 page.
*Zest Labs, Inc.* v *Walmart*; ECF No. 102-04; Walmart; "Exhibit D"; United States District Court for the Eastern District of Arkansas; Case No. 4:18-CV-00500-JM; Feb. 20, 2019; pp. 1-10.
*Zest Labs, Inc.* v *Walmart*; ECF No. 102-06; Zest Labs, Inc. et al.; "Exhibit F Filed Under Seal"; United States District Court for the Eastern District of Arkansas; Case No. 4:18-CV-00500-JM; Feb. 20, 2019; 1 page.
*Zest Labs, Inc.* v *Walmart*; ECF No. 102-07; Zest Labs, Inc. et al.; "Exhibit G Filed Under Seal"; United States District Court for the Eastern District of Arkansas; Case No. 4:18-CV-00500-JM; Feb. 20, 2019; 1 page.
*Zest Labs, Inc.* v *Walmart*; ECF No. 102-08; Williams, Fred I.; "Exhibit H"; United States District Court for the Eastern District of Arkansas; Case No. 4:18-CV-00500-JM; Feb. 20, 2019; pp. 1-5.
*Zest Labs, Inc.* v *Walmart*; ECF No. 102-09; Simons, Michael; "Exhibit I"; United States District Court for the Eastern District of Arkansas; Case No. 4:18-CV-00500-JM; Feb. 20, 2019; pp. 1-8.
*Zest Labs, Inc.* v *Walmart*; ECF No. 102-10; Williams, Fred I.; "Exhibit J"; United States District Court for the Eastern District of Arkansas; Case No. 4:18-CV-00500-JM; Feb. 20, 2019; pp. 1-4.
*Zest Labs, Inc.* v *Walmart*; ECF No. 102-11; Simons, Michael; "Exhibit K"; United States District Court for the Eastern District of Arkansas; Case No. 4:18-CV-00500-JM; Feb. 20, 2019; pp. 1-2.
*Zest Labs, Inc.* v *Walmart*; ECF No. 102-12; Tulin, Edward L.; "Exhibit L"; United States District Court for the Eastern District of Arkansas; Case No. 4:18-CV-00500-JM; Feb. 20, 2019; pp. 1-4.
*Zest Labs, Inc.* v *Walmart*; ECF No. 102-13; Sammi, P. Anthony; "Exhibit M"; United States District Court for the Eastern District of Arkansas; Case No. 4:18-CV-00500-JM; Feb. 20, 2019; pp. 1-3.
*Zest Labs, Inc.* v *Walmart*; ECF No. 102-14; Sammi, P. Anthony; "Exhibit N"; United States District Court for the Eastern District of Arkansas; Case No. 4:18-CV-00500-JM; Feb. 20, 2019; pp. 1-3.
*Zest Labs, Inc.* v *Walmart*; ECF No. 102; Zest Labs, Inc. et al.; "Plaintiffs' Motion To Compel Supplemental Responses To Interrogatories and Requests for Production From Defendant"; United States District Court for the Eastern District of Arkansas; Case No. 4:18-CV-00500-JM; Feb. 20, 2019; pp. 1-6.
*Zest Labs, Inc.* v *Walmart*; ECF No. 103; Zest Labs, Inc. et al.; "Plaintiffs' Brief in Support of Motion To Compel Supplemental Responses To Interrogatories and Requests for Production From Defendant"; United States District Court for the Eastern District of Arkansas; Case No. 4:18-CV-00500-JM; Feb. 20, 2019; pp. 1-24.
*Zest Labs, Inc.* v *Walmart*; ECF No. 105-1; Walmart; "Exhibit A—Filed Under Seal Pursuant To Order Dated Sep. 7, 2018"; United States District Court for the Eastern District of Arkansas; Case No. 4:18-CV-00500-JM; Feb. 25, 2019; 1 page.
*Zest Labs, Inc.* v *Walmart*; ECF No. 105; Walmart; "Defendant's Response To Plaintiffs' Motion To Compel"; United States District Court for the Eastern District of Arkansas; Case No. 4:18-CV-00500-JM; Feb. 25, 2019; pp. 1-21.
*Zest Labs, Inc.* v *Walmart*; ECF No. 125; Zest Labs, Inc. et al.; "Plaintiffs' Motion To Compel Defendant Walmart To Comply With the Court's Mar. 6, 2019 Order and Otherwise Produce Technical Discovery"; United States District Court for the Eastern District of Arkansas; Case No. 4:18-CV-00500-JM; Apr. 22, 2019; pp. 1-9.
*Zest Labs, Inc.* v *Walmart*; ECF No. 126; Zest Labs, Inc. et al.; "Plaintiffs' Brief in Support of Motion To Compel Defendant Walmart To Comply With the Court's Mar. 6, 2019 Order and Otherwise Produce Technical Discovery"; United States District Court for the Eastern District of Arkansas; Case No. 4:18-CV-00500-JM; Apr. 22, 2019; pp. 1-21.
*Zest Labs, Inc.* v *Walmart*; ECF No. 130-1; Sammi, P. Anthony; "Zest V. Walmart: Mar. 29, 2019 M. Simons Letter To P. Sammi Re Deficient Production of Technical Documents"; United States District Court for the Eastern District of Arkansas; Case No. 4:18-CV-00500-JM; May 8, 2019; pp. 1-2.
*Zest Labs, Inc.* v *Walmart*; ECF No. 130-2; Tulin, Edward L.; "Zest V. Walmart: Deposition Notices"; United States District Court for the Eastern District of Arkansas; Case No. 4:18-CV-00500-JM; May 8, 2019; pp. 1-2.
*Zest Labs, Inc.* v *Walmart*; ECF No. 130-3; Simons, Michael; "Zest V. Walmart: Deposition Notices"; United States District Court for the Eastern District of Arkansas; Case No. 4:18-CV-00500-JM; May 8, 2019; pp. 1-3.
*Zest Labs, Inc.* v *Walmart*; ECF No. 130-4; Walmart; "Exhibit D—Filed Under Seal Pursuant To Order Dated Sep. 7, 2018"; United States District Court for the Eastern District of Arkansas; Case No. 4:18-CV-00500-JM; May 8, 2019; 1 page.
*Zest Labs, Inc.* v *Walmart*; ECF No. 130-5; Simons, Michael; "*Zest Labs*v. *Walmart*—Walmart's Apr. 5, 2019 Production"; United States District Court for the Eastern District of Arkansas; Case No. 4:18-CV-00500-JM; May 8, 2019; pp. 1-2.
*Zest Labs, Inc.* v *Walmart*; ECF No. 130; Walmart; "Defendant's Response To Plaintiffs' Motion To Compel Compliance With the

(56) References Cited

OTHER PUBLICATIONS

Mar. 6, 2019 Order and Technical Discovery"; United States District Court for the Eastern District of Arkansas; Case No. 4:18-CV-00500-JM; May 8, 2019; pp. 1-26.
*Zest Labs, Inc.* v *Walmart*; ECF No. 131-1; Walmart; "Exhibit A—Filed Under Seal Pursuant To Order Dated Sep. 7, 2018"; United States District Court for the Eastern District of Arkansas; Case No. 4:18-CV-00500-JM; May 8, 2019; 1 page.
*Zest Labs, Inc.* v *Walmart*; ECF No. 131-2; Walmart; "Exhibit B—Filed Under Seal Pursuant To Order Dated Sep. 7, 2018"; United States District Court for the Eastern District of Arkansas; Case No. 4:18-CV-00500-JM; May 8, 2019; 1 page.
*Zest Labs, Inc.* v *Walmart*; ECF No. 131-3; Sammi, P. Anthony; "RE: 4:18-CV-00500-JM *Zest Labs Inc et al* v. *Wal-Mart Inc*"; United States District Court for the Eastern District of Arkansas; Case No. 4:18-CV-00500-JM; May 8, 2019; 1 page.
*Zest Labs, Inc.* v *Walmart*; ECF No. 131-4; Simons, Michael; "RE: 4:18-CV-00500-JM *Zest Labs Inc et al* v. *Wal-Mart Inc*"; United States District Court for the Eastern District of Arkansas; Case No. 4:18-CV-00500-JM; May 8, 2019; 1 page.
*Zest Labs, Inc.* v *Walmart*; ECF No. 131; Walmart; "Defendant's Sur-Reply Brief in Further Opposition To Plaintiffs' Motion To Compel"; United States District Court for the Eastern District of Arkansas; Case No. 4:18-CV-00500-JM; May 8, 2019; pp. 1-21.
*Zest Labs, Inc.* v *Walmart*; ECF No. 250; Walmart; "Defendant's Reply Brief in Support of Its Motion To Exclude Proposed Expert Testimony of Patent Attorney Q. Todd Dickinson"; United States District Court for the Eastern District of Arkansas; Case No. 4:18-CV-00500-JM; Mar. 27, 2020; pp. 1-13.
*Zest Labs, Inc.* v *Walmart*; ECF No. 257-1; Walmart; "Defendant's Surreply in Further Opposition To Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Mar. 31, 2020; pp. 1-168.
*Zest Labs, Inc.* v *Walmart*; ECF No. 257-1; Walmart; "Defendant's Surreply in Further Opposition To Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Mar. 31, 2020; pp. 169-336.
*Zest Labs, Inc.* v *Walmart*; ECF No. 257-1; Walmart; "Defendant's Surreply in Further Opposition To Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Mar. 31, 2020; pp. 337-342.
*Zest Labs, Inc.* v *Walmart*; ECF No. 257; Walmart; "Defendant's Motion for Leave To File Surreply in Further Opposition To Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Mar. 31, 2020; pp. 1-3.
*Zest Labs, Inc.* v *Walmart*; ECF No. 261-1; Blitzer, Rachel R.; "Declaration of Rachel R. Blitzer Regarding Walmart's Surreply in Further Opposition To Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Apr. 6, 2020; pp. 1-169.
*Zest Labs, Inc.* v *Walmart*; ECF No. 261-1; Blitzer, Rachel R.; "Declaration of Rachel R. Blitzer Regarding Walmart's Surreply in Further Opposition To Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Apr. 6, 2020; pp. 170-337.
*Zest Labs, Inc.* v *Walmart*; ECF No. 261; Walmart; "Defendant's Surreply in Further Opposition To Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Apr. 6, 2020; pp. 1-5.
*Zest Labs, Inc.* v *Walmart*; ECF No. 262; Walmart; "Brief in Support of Defendant's Motion for Summary Judgment"; United States District Court for the Eastern District of Arkansas; Case No. 4:18-CV-00500-JM; Apr. 21, 2020; pp. 1-54.
*Zest Labs, Inc.* v *Walmart*; ECF No. 263; Walmart; "Defendant's Motion To Exclude Certain Proposed Expert Testimony of Mark Lanning"; United States District Court for the Eastern District of Arkansas; Case No. 4:18-CV-00500-JM; Apr. 21, 2020; pp. 1-6.
*Zest Labs, Inc.* v *Walmart*; ECF No. 264; Walmart; "Brief in Support of Defendant's Motion To Exclude Proposed Expert Testimony of Mark Lanning"; United States District Court for the Eastern District of Arkansas; Case No. 4:18-CV-00500-JM; Apr. 21, 2020; pp. 1-26.
*Zest Labs, Inc.* v *Walmart*; ECF No. 265; Walmart; "Defendant's Motion To Exclude Testimony of Damages Expert Stephen L. Becker, Ph.D."; United States District Court for the Eastern District of Arkansas; Case No. 4:18-CV-00500-JM; Apr. 21, 2020; pp. 1-7.
*Zest Labs, Inc.* v *Walmart*; ECF No. 266; Walmart; "Brief in Support of Defendant's Motion To Exclude Testimony of Damages Expert Stephen L. Becker, Ph.D."; United States District Court for the Eastern District of Arkansas; Case No. 4:18-CV-00500-JM; Apr. 21, 2020; pp. 1-22.
*Zest Labs, Inc.* v *Walmart*; ECF No. 267; Walmart; "Defendant's Response To Zest Labs, Inc.'s Motion for Summary Judgment That Information in Walmart's Patent Application Was Not Generally Known or Readily Ascertainable"; United States District Court for the Eastern District of Arkansas; Case No. 4:18-CV-00500-JM; Apr. 21, 2020; pp. 1-23.
*Zest Labs, Inc.* v *Walmart*; ECF No. 268; Walmart; "Defendant's Response To Zest Labs, Inc.'s Motion for Partial Summary Judgment That Walmart Used and Disclosed Zest Labs' Information in the Walmart Applications"; United States District Court for the Eastern District of Arkansas; Case No. 4:18-CV-00500-JM; Apr. 21, 2020; pp. 1-29.
*Zest Labs, Inc.* v *Walmart*; ECF No. 269; Walmart; "Defendant's Response To Plaintiffs' Motion To Exclude Testimony of Walmart's Damages Expert, Dr. William Choi"; United States District Court for the Eastern District of Arkansas; Case No. 4:18-CV-00500-JM; Apr. 21, 2020; pp. 1-17.
*Zest Labs, Inc.* v *Walmart*; ECF No. 270; Walmart; "Defendant's Response To Plaintiffs' Motion To Exclude Testimony of Walmart's Technical Expert, Dr. David Dobkin, Ph.D."; United States District Court for the Eastern District of Arkansas; Case No. 4:18-CV-00500-JM; Apr. 21, 2020; pp. 1-13.
*Zest Labs, Inc.* v *Walmart*; ECF No. 271; Walmart; "Defendant's Response To Plaintiffs' Motion To Exclude Testimony of Walmart's Technical Expert, Dr. Catherine Adams Hutt, Ph.D."; United States District Court for the Eastern District of Arkansas; Case No. 4:18-CV-00500-JM; Apr. 21, 2020; pp. 1-25.
*Zest Labs, Inc.* v *Walmart*; ECF No. 272; Walmart; "Defendant's Reply Brief in Support of Its Motion To Exclude Testimony of Damages Expert Stephen L. Becker, Ph.D."; United States District Court for the Eastern District of Arkansas; Case No. 4:18-CV-00500-JM; Apr. 21, 2020; pp. 1-22.
*Zest Labs, Inc.* v *Walmart*; ECF No. 273; Walmart; "Defendant's Reply Brief in Support of Its Motion for Summary Judgment"; United States District Court for the Eastern District of Arkansas; Case No. 4:18-CV-00500-JM; Apr. 21, 2020; pp. 1-56.
*Zest Labs, Inc.* v *Walmart*; ECF No. 274; Walmart; "Defendant's Reply Brief in Support of Its Motion To Exclude Proposed Expert Testimony of Mark Lanning"; United States District Court for the Eastern District of Arkansas; Case No. 4:18-CV-00500-JM; Apr. 21, 2020; pp. 1-22.
*Zest Labs, Inc.* v *Walmart*; ECF No. 275; Zest Labs, Inc. et al.; "Zest Labs Inc.'s Motion for Partial Summary Judgment That Walmart Used and Disclosed Zest's Information in the Walmart Applications"; United States District Court for the Eastern District of Arkansas; Case No. 4:18-CV-00500-JM; Apr. 21, 2020; pp. 1-4.
*Zest Labs, Inc.* v *Walmart*; ECF No. 276; Zest Labs, Inc. et al.; "Plaintiffs' Motion To Exclude Testimony of Walmart's Expert, Dr.

(56) References Cited

OTHER PUBLICATIONS

David P. Dobkin"; United States District Court for the Eastern District of Arkansas; Case No. 4:18-CV-00500-JM; Apr. 21, 2020; pp. 1-3.

Zest Labs, Inc. v Walmart; ECF No. 277; Zest Labs, Inc. et al.; "Brief in Support of Plaintiffs' Motion To Exclude the Testimony of Walmart's Expert Witness, Dr. David P. Dobkin"; United States District Court for the Eastern District of Arkansas; Case No. 4:18-CV-00500-JM; Apr. 21, 2020; pp. 1-59.

Zest Labs, Inc. v Walmart; ECF No. 278; Zest Labs, Inc. et al.; "Plaintiffs' Motion To Exclude Testimony of Walmart Expert, Dr. Catherine Adams Hutt"; United States District Court for the Eastern District of Arkansas; Case No. 4:18-CV-00500-JM; Apr. 21, 2020; pp. 1-4.

Zest Labs, Inc. v Walmart; ECF No. 279; Zest Labs, Inc. et al.; "Brief in Support of Plaintiffs' Motion To Exclude the Testimony of Walmart's Expert Witness, Dr. Catherine Adams Hutt"; United States District Court for the Eastern District of Arkansas; Case No. 4:18-CV-00500-JM; Apr. 21, 2020; pp. 1-64.

Zest Labs, Inc. v Walmart; ECF No. 280; Zest Labs, Inc. et al.; "Zest Labs Inc.'s Motion for Partial Summary Judgment That Information in Walmart's Patent Application Was Not Generally Known or Readily Ascertainable"; United States District Court for the Eastern District of Arkansas; Case No. 4:18-CV-00500-JM; Apr. 21, 2020; pp. 1-4.

Zest Labs, Inc. v Walmart; ECF No. 281; Zest Labs, Inc. et al.; "Plaintiffs' Motion To Exclude Testimony of Walmart's Damages Expert, Dr. William Choi"; United States District Court for the Eastern District of Arkansas; Case No. 4:18-CV-00500-JM; Apr. 21, 2020; pp. 1-4.

Zest Labs, Inc. v Walmart; ECF No. 282; Zest Labs, Inc. et al.; "Plaintiffs' Brief in Support of Motion To Exclude Testimony of Walmart's Damages Expert, Dr. William Choi"; United States District Court for the Eastern District of Arkansas; Case No. 4:18-CV-00500-JM; Apr. 21, 2020; pp. 1-30.

Zest Labs, Inc. v Walmart; ECF No. 283; Zest Labs, Inc. et al.; "Zest Labs Inc.'s Brief in Support of Its Motion for Partial Summary Judgment That Information in Walmart's Patent Application Was Not Generally Known or Readily Ascertainable"; United States District Court for the Eastern District of Arkansas; Case No. 4:18-CV-00500-JM; Apr. 21, 2020; pp. 1-159.

Zest Labs, Inc. v Walmart; ECF No. 284; Zest Labs, Inc. et al.; "Zest Labs Inc.'s Brief in Support of Its Motion for Partial Summary Judgment That Walmart Used and Disclosed Zest Labs' Information in the Walmart Applications"; United States District Court forthe Eastern District of Arkansas; Case No. 4:18-CV-00500-JM; Apr. 21, 2020; pp. 1-165.

Zest Labs, Inc. v Walmart; ECF No. 285; Zest Labs, Inc. et al.; "Zest Labs Inc.'s Motion for Summary Judgment On Its Claim for Breach of Contract"; United States District Court for the Eastern District of Arkansas; Case No. 4:18-CV-00500-JM; Apr. 21, 2020; pp. 1-3.

Zest Labs, Inc. v Walmart; ECF No. 286; Zest Labs, Inc. et al.; "Zest Labs Inc.'s Brief in Support of Its Motion for Summary Judgment On Its Claim for Breach of Contract"; United States District Court for the Eastern District of Arkansas; Case No. 4:18-CV-00500-JM; Apr. 21, 2020; pp. 1-30.

Zest Labs, Inc. v Walmart; ECF No. 287; Zest Labs, Inc. et al.; "Plaintiffs' Response To Defendant's Motion for Summary Judgment"; United States District Court for the Eastern District of Arkansas; Case No. 4:18-CV-00500-JM; Apr. 21, 2020; pp. 1-138.

Zest Labs, Inc. v Walmart; ECF No. 288; Zest Labs, Inc. et al.; "Plaintiffs' Opposition To Defendant's Motion To Exclude Testimony of Damages Expert Stephen L. Becker, Ph.D."; United States District Court for the Eastern District of Arkansas; Case No. 4:18-CV-00500-JM; Apr. 21, 2020; pp. 1-63.

Zest Labs, Inc. v Walmart; ECF No. 289; Zest Labs, Inc. et al.; "Plaintiffs' Brief in Opposition of Defendant's Motion To Exclude Proposed Expert Testimony of Patent Attorney Q. Todd Dickinson"; United States District Court for the Eastern District of Arkansas; Case No. 4:18-CV-00500-JM; Apr. 21, 2020; pp. 1-180.

Zest Labs, Inc. v Walmart; ECF No. 290; Zest Labs, Inc. et al.; "Plaintiffs' Brief in Opposition of Defendant's Motion To Exclude Proposed Expert Testimony of Mark Lanning"; United States District Court for the Eastern District of Arkansas; Case No. 4:18-CV-00500-JM; Apr. 21, 2020; pp. 1-62.

Zest Labs, Inc. v Walmart; ECF No. 291; Zest Labs, Inc. et al.; "Zest Labs Inc.'s Reply Brief in Support of Its Motion for Partial Summary Judgment That Information in Walmart's Patent Application Was Not Generally Known or Readily Ascertainable"; United States District Court for the Eastern District of Arkansas; Case No. 4:18-CV-00500-JM; Apr. 21, 2020; pp. 1-18.

Zest Labs, Inc. v Walmart; ECF No. 292; Zest Labs, Inc. et al.; "Plaintiffs' Reply in Support of Their Motion To Exclude Testimony of Walmart's Damages Expert Dr. William Choi"; United States District Court for the Eastern District of Arkansas; Case No. 4:18-CV-00500-JM; Apr. 21, 2020; pp. 1-20.

Zest Labs, Inc. v Walmart; ECF No. 293; Zest Labs, Inc. et al.; "Brief in Support of Plaintiffs' Motion To Exclude the Testimony of Walmart's Expert Witness, Dr. David P. Dobkin"; United States District Court for the Eastern District of Arkansas; Case No. 4:18-CV-00500-JM; Apr. 21, 2020; pp. 1-13.

Zest Labs, Inc. v Walmart; ECF No. 294; Zest Labs, Inc. et al.; "Zest Labs Inc.'s Reply in Support of Their Motion for Partial Summary Judgment That Walmart Used and Disclosed Zest's Information in the Walmart Application"; United States District Court for the Eastern District of Arkansas; Case No. 4:18-CV-00500-JM; Apr. 21, 2020; pp. 1-39.

Zest Labs, Inc. v Walmart; ECF No. 295; Zest Labs, Inc. et al.; "Plaintiffs' Reply in Support of Their Motion To Exclude the Testimony of Walmart's Expert Witness, Dr. Catherine Adams Hutt"; United States District Court for the Eastern District of Arkansas; Case No. 4:18-CV-00500-JM; Apr. 21, 2020; pp. 1-23.

Zest Labs, Inc. v Walmart; ECF No. 296; Zest Labs, Inc. et al.; "Plaintiffs' Objections To and Motion To Strike Evidence Cited in Walmart's Responses To Zest Labs, Inc.'s Statement of Material Facts in Support of Its Motions for Partial for Summary Judgement and Motion for Summary Judgment"; United States District Court for the Eastern District of Arkansas; Case No. 4:18-CV-00500-JM; Apr. 21, 2020; pp. 1-5.

Zest Labs, Inc. v Walmart; ECF No. 297; Zest Labs, Inc. et al.; "Plaintiffs' Memorandum in Support of Objections To and Motion To Strike Evidence Cited in Walmart's Responses To Zest Labs, Inc.'s Statement of Material Facts in Support of Its Motions for Partial for Summary Judgement and Motion for Summary Judgment"; United States District Court for the Eastern District of Arkansas; Case No. 4:18-CV-00500-JM; Apr. 21, 2020; pp. 1-5.

Zest Labs, Inc. v Walmart; ECF No. 298; Walmart; "Defendant's Consolidated Brief in Opposition To Plaintiffs' Objections To and Motions To Strike Evidence Cited By Walmart in Connection With Summary Judgment Motions (Dkts. 222 & 248)"; United States District Court for the Eastern District of Arkansas; Case No. 4:18-CV-00500-JM; May 4, 2020; pp. 1-18.

Haard, Norman F., et al.; "Characteristics of Edible Plant Tissues"; Food Chemistry, edited by Owen R. Fennema; 3rd Ed.; Marcel Dekker, Inc.; 1996; pp. 943-1011.

Haugen, John E., et al.; "Application of gas-sensor array technology for detection and monitoring of growth of spoilage bacteria in milk: A model study"; Analytics Chimica Acta; vol. 565, No. 1; https://doi.org/10.1016/j.aca.2006.02.016; Feb. 23, 2006; pp. 10-16.

Kader, Adel A., et al.; "Technologies to Extend the Refrigerated Shelf Life of Fresh Fruit"; Food Storage Stability, edited by Irwin A. Taub, et al.; Boca Raton; CRC Press; 1998; pp. 1-27.

Kader, Adel A.; "Postharvest Technology of Horticultural Crops"; 2002; 3rd Ed.; University of California Agriculture and Natural Resources; Oakland; 56 pages.

Kader, Adel A.; "Postharvest Technology of Horticultural Crops"; 2002; 3rd Ed.; University of California Agriculture and Natural Resources; Oakland; 74 pages.

Kader, Adel A.; "Postharvest Technology of Horticultural Crops"; 2002; 3rd Ed.; University of California Agriculture and Natural Resources; Oakland; pp. 113-196.

(56) References Cited

OTHER PUBLICATIONS

Kader, Adel A.; "Postharvest Technology of Horticultural Crops"; 2002; 3rd Ed.; University of California Agriculture and Natural Resources; Oakland; pp. 197-250.
Kader, Adel A.; "Postharvest Technology of Horticultural Crops"; 2002; 3rd Ed.; University of California Agriculture and Natural Resources; Oakland; pp. 251-314.
Kader, Adel A.; "Postharvest Technology of Horticultural Crops"; 2002; 3rd Ed.; University of California Agriculture and Natural Resources; Oakland; pp. 315-384.
Kader, Adel A.; "Postharvest Technology of Horticultural Crops"; 2002; 3rd Ed.; University of California Agriculture and Natural Resources; Oakland; pp. 385-434.
Kader, Adel A.; "Postharvest Technology of Horticultural Crops"; 2002; 3rd Ed.; University of California Agriculture and Natural Resources; Oakland; pp. 435-480.
Kader, Adel A.; "Postharvest Technology of Horticultural Crops"; 2002; 3rd Ed.; University of California Agriculture and Natural Resources; Oakland; pp. 67-112.
Kong, F. et al.; "Chemical Deterioration and Physical Instability of Foods and Beverages"; The Stability and Shelf Life of Food, edited by Persis Subramaniam; 2nd Ed.; Woodhead Publishing; 2016; pp. 1-21.
Labuza, T. P., et al.; "The Relationship Between Processing and Shelf Life"; Foods for the '90s, edited by Gordon G. Birch, et al.; Elsevier Applied Science; Aug. 1, 1990; pp. 1-21.
Robertson, Gordon L.; "Food Packaging: Principles and Practice"; 3rd Ed.; Boca Raton; CRC Press; 2013; pp. 1-33.
Singh, R. P.; "Scientific Principles of Shelf-Life Evaluation"; Shelf-Life Evaluation of Foods, edited by Dominic Man, et al.; 2nd Ed.; Aspen Publishers, Inc.; 2000; pp. 1-23.
Singh, R. Paul et al.; "Introduction to Food Engineering"; 5th Ed.; Academic Press; 2014; pp. 1-31.
Wells, John H. et al.; "Quality Management During Storage and Distribution"; Food Storage Stability, edited by Irwin A. Taub, et al.; Boca Raton; CRC Press; 1998; pp. 1-29.
Wells, John H., et al.; "Temperature Tolerance of Foods during Distribution"; Handbook of Food Engineering Practice, edited by Kenneth J. Valentas, et al.; Boca Raton; CRC Press; 1997; pp. 1-29.
Wells, John H., et al.; "The Application of Time-Temperature Indicator Technology to Food Quality Monitoring and Perishable Inventory Management"; Mathematical Modelling of Food Processing Operations, edited by Stuart Thorne; Elsevier Applied Science; 1992; pp. 1-41.
National Geographic Society, Season, Sep. 22, 2016 (Year: 2016).
Andrew Wilson, "Vision Software Blends into Food Processing", Jun. 1, 2012, pp. 1-13.
International Search Report and Written Opinion dated Nov. 4, 2019 in International Application No. PCT/US2019/043461; pp. 1-7.
ReFED; "Retail Food Waste Action Guide"; https://www.refed.com/downloads/Retail_Guide_Web.pdf; 2018; pp. 1-44.
S. Mandal et al., "Optimal production inventory policy for defective items with fuzzy lime period", Science Direct, Applied Mathematical modelling, vol. 34, Issue 3, Mar. 2010, pp. 1-27.
S. Ren, K. He, R. Girshick, and J. Sun. Faster R-CNN: Towards real-time object detection with region proposal networks. In NIPS, 2015. (Year: 2015); pp. 1-9.
Zest Labs; "On-demand meal quality visibility from the restaurant to consumer delivery"; https://www.zestlabs.com/zest-delivery/; Available as early as Oct. 22, 2017; pp. 1-7.

\* cited by examiner

SYSTEMS AND METHODS FOR ASSESSING PRODUCTS

CROSS-REFERENCE TO RELATED APPLICATION

This application claims the benefit of Indian Provisional Application No. 201841043606, filed Nov. 20, 2018, and U.S. Provisional Application No. 62/810,129, filed Feb. 25, 2019, which are incorporated by reference in their entirety herein.

TECHNICAL FIELD

This invention relates generally to product assessment and, more particularly, product assessment by a retailer.

BACKGROUND

Many products require inspection by a retailer before the products are offered for sale to consumers. For example, the retailer may inspect the products for defects, damage, quantity, etc. so as to ensure that only suitable products are offered for sale to consumers. This inspection processed is typically done manually. For example, an employee will physically inspect all, or a sample, of the products to determine if the products are suitable for sale. While manual inspection of products can be used to determine the quality of products, it is time-consuming, and thus costly, for retailers. Additionally, manual inspection can be error prone due to the subjective nature of the inspection as well as potential employee fatigue and/or oversight. Consequently, a need exists for systems, methods, and apparatuses that can quickly, accurately, and consistently inspect products.

BRIEF DESCRIPTION OF THE DRAWINGS

Disclosed herein are embodiments of systems, apparatuses, and methods pertaining to assessing products. This description includes drawings, wherein.

Figure 1A:
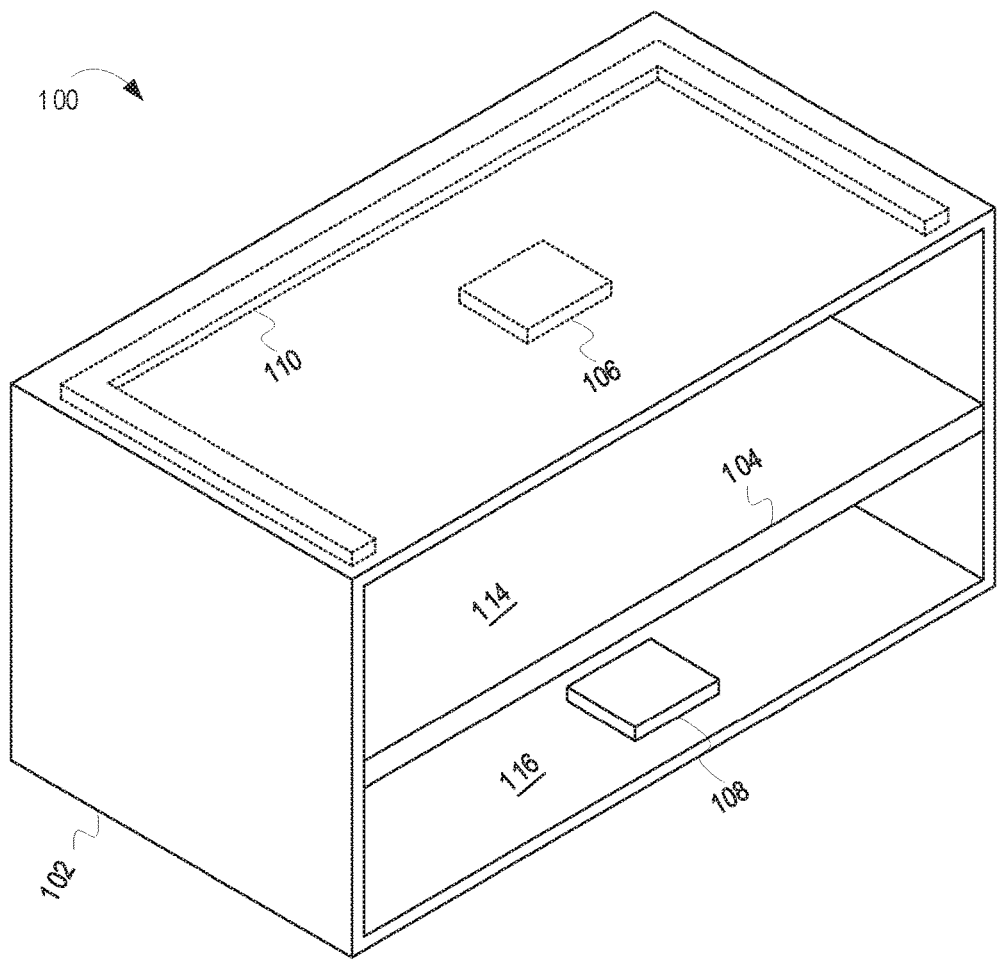
FIG. 1A is an isometric view of an enclosure 100 for assessing products, according to some embodiments.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to various embodiments, systems, apparatuses, and methods are provided herein useful to an enclosure for use in assessing products. In some embodiments, an enclosure for use in assessing products comprises a housing, wherein the housing includes a door configured to allow placement of a product within the housing, a product holding surface, wherein the product holding surface is located within the housing, wherein the product holding surface allows pictures to be taken through the product holding surface, wherein the product holding surface divides the housing into a first portion and a second portion, and wherein the product holding surface is configured to support the product, a first image capture device, wherein the first image capture device is located within the first portion of the housing, and wherein the first image capture device is configured to capture an image of the product from a first perspective, a second image capture device, wherein the second image capture device is located within the second portion of the housing, wherein the second image capture device is configured to capture an image of the product from a second perspective, and wherein the image of the product from the second perspective is captured through the product holding surface, and a lighting element, wherein the lighting element is located within the housing, and wherein the lighting element is configured to provide lighting within the housing.

As previously discussed, many retailers inspect products received from suppliers, manufacturers, etc. before they offer the products for sale to consumers. This inspection is performed to ensure that only suitable products are offered for sale. Not only does this aid the retailer in promoting his or her reputation as a seller of quality goods, but some product inspections are required by governmental agencies (e.g., the Food and Drug Administration (FDA)). In addition to ensuring that only suitable products are offered for sale, the retailer may benefit from this inspection in that he or she may reject products that are not suitable for sale and thus avoid paying for products that are not suitable for sale.

Currently, many retailers perform these inspections manually. This manual inspection is time-consuming and error prone. As one example, a retailer may inspect produce before offering the produce for sale. In the case of strawberries, the retailer may inspect one percent (1%) of all strawberries received in a shipment. If the retailer receives 3,000 packages (e.g., clamshells) of strawberries, the retailer must inspect 30 of the packages. To inspect a package of strawberries, the employee must remove the strawberries from the package, count the strawberries, visually inspect the strawberries, determine if there is any damage (e.g., bruising, mold, etc.), quantify the damage, record the damage, and then return the strawberries to the packaging. For an experienced employee, this process can take about two minutes to complete for each package. Consequently, if 30 packages of strawberries are to be inspected, this process will take about an hour. When adding this time amongst all other products that are to be inspected, it is easy to see how the inspection of products can require a significant portion of a retailer's recourses.

Described herein are systems, methods, and apparatuses that can be used to help automate this inspection process. Specifically, described herein are enclosures, and methods for using such enclosures, to automate the inspection process. Such enclosures and methods can be used in conjunction with automated evaluation techniques (e.g., an automated inspection system), such as those described in U.S.

Provisional Appl. No. 62/509,945, which is incorporated herein by reference in its entirety. Generally, the enclosure is capable of accepting a product and includes an image capture device. The image capture device captures an image of the product under controlled conditions. In some embodiments, the image of the product is transmitted to an external system, such as that described in U.S. Provisional Application No. 62/509,945 for an automated analysis (e.g., scoring) of the product. The discussion of FIGS. 1A and 1B provide an overview of such an enclosure.

Figure 1B:
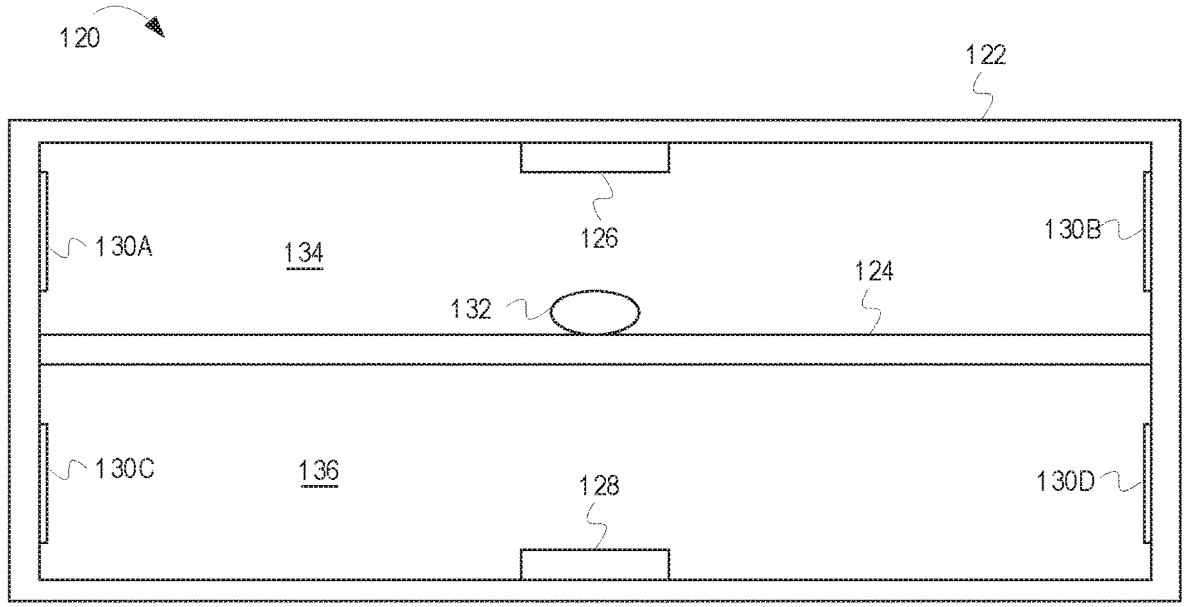
FIG. 1B is a frontal view of an enclosure 120 for assessing products, according to some embodiments.

FIG. 1A is an isometric view of an enclosure 100 for assessing products, according to some embodiments. The enclosure includes a housing 102. Generally, the housing 102 is a box capable of having a product placed within the enclosure 100. While the housing 102 depicted in FIG. 1A is a rectangular prism-shape, such is not required. That is, any shape suitable for receiving (i.e., allowing placement of) a product can be used and the shape of the housing 102 can be based upon the product being inspected.

The housing 102 includes a door (not shown). The door can be of any suitable type. For example, the door can be hinged at one, or multiple, ends of the housing 102, be slidable across the housing 102, rotate within or around the housing 102, foldable within or about the housing, etc. The door can be rigid and/or pliable (e.g., fabric), as desired based on the type of the enclosure 100 and/or the products being assessed. The door can take any suitable form based on a desired condition within the housing 102. For example, in some embodiments, it may be desired that the door create a seal with the housing 102 that prevents, or diminishes the amount of, external light entering the housing 102 when closed. It should be noted, that in some embodiments, the door may not be a "door" in the traditional sense, but rather a "doorway" into the enclosure. That is, the door may simply be an opening in the housing 102 that allows placement of a product in the housing 102.

The housing 102 includes a product holding surface 104. The product holding surface 104 is configured to support the product. The product holding surface 104 divides the housing 102 into two portions: a first portion 114 and a second portion 116. Although the product holding surface 104 roughly divides the housing 102 into two equal portions (i.e., the first portion 114 is roughly the same size as the second portion 116) in FIG. 1A, such is not required. Additionally, in some embodiments, the height of the product holding surface 104 can be adjusted within the housing 102 to accommodate products of different sizes and/or fine-tune how images of the product are captured (i.e., the product holding surface 104 is moveable). Preferably, the product holding surface 104 comprises a transparent or translucent material through which images of the product can be taken (i.e., the product holding surface 104 is substantially transparent). For example, the product holding surface 104 can be made of glass, plastic, and/or any other suitable material. Additionally, in some embodiments, only a portion of the product holding surface 104 may allow images to be captured through the product holding surface. For example, only a portion, such as a window, may be transparent or translucent and the remainder of the product holding surface 104 opaque.

In some embodiments, the product holding surface 104 includes a product barrier. The product barrier is configured to retain products placed on the product holding surface 104 in a specified area (e.g., in the field of view of an image capture device, optimally placed for the capturing of images, on the product holding surface 104, etc.). The product barrier can comprise any suitable structure, mechanism, or device for positioning of the product holding surface 104. For example, the product barrier can include an incline (e.g., the product holding surface 104, a portion of the product holding surface 104, or a structure associated with the product holding surface 104 can be inclined), a ledge, a ridge, a wall, etc.

The enclosure 100 includes two image capture devices: a first image capture device 106 and a second image capture device 108. The image capture devices can be of any suitable type and are capable of capture still and/or moving images (e.g., video). The image capture devices can be selected based on the size of the housing 102, type of products to be assessed, placement of the product holding surface 104, the shape of the housing 102, the type(s) of images desired, etc. For example, the image capture devices can include wide angle lenses to capture a large area of the housing 102.

The first image capture device 106 is located in the first portion 114 of the housing 102 and is configured to capture images of products from a first perspective. As depicted in FIG. 1A, the first image capture device 106 is positioned to capture an overhead image of the product. That is, the first image capture device 106 is located on the "ceiling" of the housing 102, as indicated by the dashed lines. Although FIG. 1A depicts the first image capture device 106 as being located on the "ceiling" of the housing 102, such is not required. That is, the first image capture device 106 can be located anywhere in the first portion 114 of the housing 102. For example, the first image capture device 106 can be located on wall of the housing 102 (e.g., the side or back of the housing 102) to capture images of products from the side. The first image capture device 106 can be located anywhere within the first portion 114 of the housing 102, as required to capture desired images of products.

The second image capture device 108 is located in the second portion 116 of the housing 102 and is configured to capture images of products from a second perspective. As depicted in FIG. 1A, the second image capture device 108 is located on the "floor" of the housing 102. In such embodiments, the second image capture device 108 captures images of products through the product holding surface 104. That is, the second image capture device 108 captures images of the product from a second perspective that is through the product holding surface 104. Although the second image capture device 108 is depicted in FIG. 1A as being on the "floor" of the housing 102, such is not required. For example, the second image capture device 108 can be located on a wall or the back of the housing 102. The second image capture device 108 can be located anywhere within the second portion 116 of the housing 102, as required to capture desired images of products.

Additionally, though FIG. 1A depicts only two image capture devices, in some embodiments, the enclosure 100 can include additional image capture devices. For example, the enclosure 100 can include a third image capture device to capture images of products from a third perspective, a fourth image capture device to capture images of products from a fourth perspective, etc. The additional image capture devices can be located anywhere about the enclosure 100 (e.g., in the housing 102, on the housing 102, outside of the housing 102, on a door, etc.).

In some embodiments, the enclosure 100 includes a lighting element 110. The lighting element is configured to provide lighting for the enclosure 100. In one embodiment, the lighting element 110 is located within the housing 102. In such embodiments, the lighting element 110 provides lighting within the housing 102. For example, as depicted in FIG. 1A, the lighting element 110 can be located on the "ceiling" of the housing 102, as indicated by the dashed lines. The lighting element can be of any suitable type (e.g., incandescent, fluorescent, LED, etc.) and can produce light that is visible and/or invisible to the human eye.

While FIG. 1A depicts an isometric view of an enclosure, FIG. 1B depicts a frontal view of an enclosure.

FIG. 1B is a frontal view of an enclosure 120 for assessing products, according to some embodiments. Like the enclosure depicted in FIG. 1A, the enclosure 120 depicted in FIG. 1B includes a housing 122, a door (not shown), a product holding surface 104, a first image capture device 126, a second image capture device 128, and a lighting element.

The lighting element depicted in FIG. 1B includes four lighting elements: a first lighting element 130A, a second lighting element 130B, a third lighting element 130C, and a fourth lighting element 130D. The first lighting element 130A and the second lighting element 130B are located in a first portion 134 of the housing 122. The third lighting element 130C and the fourth lighting element 130D are located in the second portion 136 of the housing 124. Although depicted as being located on the walls of the housing 122, the lighting element can be located in any suitable location to achieve the lighting effects desired. Additionally, the lighting element can include greater, or fewer (as depicted in FIG. 1A), than four lighting elements.

FIG. 1B includes a product 132 placed on the product holding surface 124. Although the product 132 is depicted as only a single item, this is done only for simplicity. The product 132 may include multiple items and can be any type of items.

Figure 2:
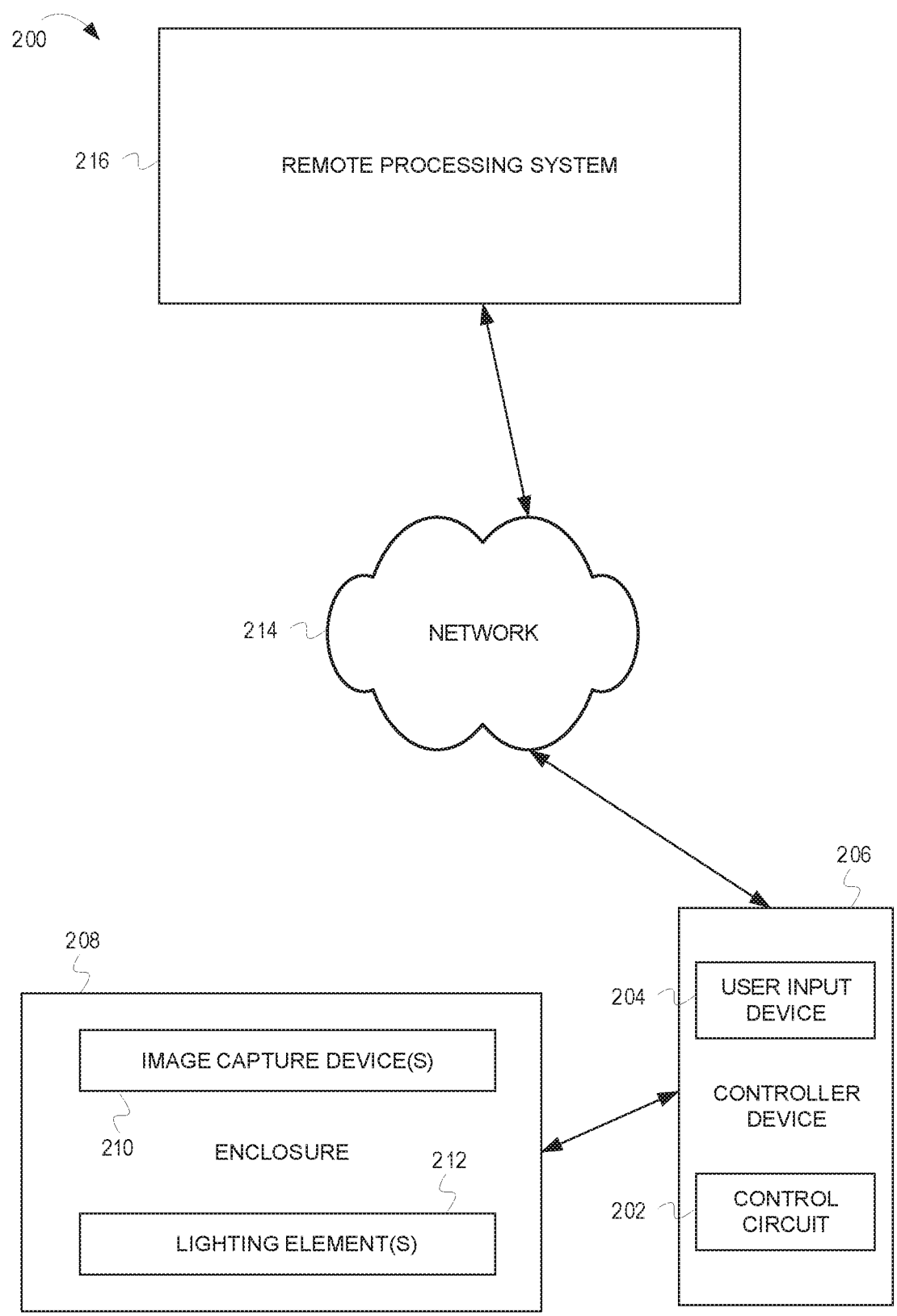
FIG. 2 is a block diagram of a system 200 for assessing products, according to some embodiments.

While the discussion of FIGS. 1A and 1B provide an overview of an enclosure for use in assessing products, the discussion of FIG. 2 provides detail regarding a system for assessing products.

FIG. 2 is a block diagram of a system 200 for assessing products, according to some embodiments. The system includes a remote processing system 216, an enclosure 208, and a controller device 206. In some embodiments, at least some of the remote processing system 216, the controller device 206, and the enclosure 208 are in communication with one another. For example, as depicted in FIG. 2, the controller device 206 and the remote processing system 216 are communicatively coupled via a network 214 (e.g., an intranet or internet, such as the Internet). Additionally, the controller device 206 is communicatively coupled to the enclosure 208. Although not being depicted as being communicatively coupled to one another via the network 214, in some embodiments, the controller device 206 and the enclosure are communicatively coupled in a wireless means, such as via the network 214, Bluetooth, etc.

The enclosure 208 is configured to allow placement of a product within the enclosure 208 for assessment. The enclosure includes an image capture device(s) 210 and lighting element(s) 212. The image capture device(s) 210 is configured to capture images of the product in the enclosure 208 and the lighting element(s) 212 is configured to provide light for capturing the images.

The controller device 206 generally controls the capture of images in the enclosure 208. The controller device 206 can be of any suitable type, such as a device dedicated to the control of the enclosure 208 (e.g., a controller designed specifically for use with the enclosure 208, whether integral or separate from the enclosure 208) or an existing device modified to control the enclosure (e.g., a mobile device or other computing device running an application to control the enclosure 208).

The controller device 206 controls the enclosure 208 by controlling the image capture capture(s) device 210 and the lighting element(s) 212. For example, the controller device 206 instructs the lighting element(s) 212 to illuminate the enclosure 208 and the image capture device(s) 210 to capture an image of the product.

The controller device 206 includes a user input device 204 and a control circuit 202. The user input device 204 allows users to input commands to the controller device 206. For example, the user input device 204 can allow the user to input commands for the image capture device(s) 210 (e.g., capture an image, move or rotate the image capture device, turn a flash on or off, etc.) and for the lighting element(s) 212 (e.g., illuminate the enclosure 208, change the color of the light, adjust the angle of the light, adjust the timing of the light, etc.).

The control circuit 202 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. The control circuit 202 is configured (for example, by using corresponding programming as will be well understood by those skilled in the art) to carry out one or more of the steps, actions, and/or functions described herein.

By one optional approach the control circuit 202 operably couples to a memory. The memory may be integral to the control circuit 202 or can be physically discrete (in whole or in part) from the control circuit 202 as desired. This memory can also be local with respect to the control circuit 202 (where, for example, both share a common circuit board, chassis, power supply, and/or housing) or can be partially or wholly remote with respect to the control circuit 202 (where, for example, the memory is physically located in another facility, metropolitan area, or even country as compared to the control circuit 202).

This memory can serve, for example, to non-transitorily store the computer instructions that, when executed by the control circuit 202, cause the control circuit 202 to behave as described herein. As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).

The control circuit 202 is configured to transmit and/or receive commands from the user input device 204, the image capture device(s) 210, the lighting element(s) 212, and the remote processing system 216. For example, the control circuit 202 can receive an execution command from the user input device. The execution command includes instructions for the control circuit 202 to control the enclosure 208. For example, the execution command can include instructions regarding when and how the image capture device(s) 210 and the lighting element(s) 212 should operate. After an image is, or images are, captured by the image capture device(s) 210, the control circuit transmits the image, or images, to the remote processing system 216.

The remote processing system 216 receives the image(s) from the controller device 206 and performs an analysis on the product. For example, the analysis on the product can be an assessment of the image(s) of the product to determine a score for the product. In some embodiments, the remote processing system 216 operates as described in U.S. Provisional Application No. 62/509,945 for an automated inspection system.

Figure 3:
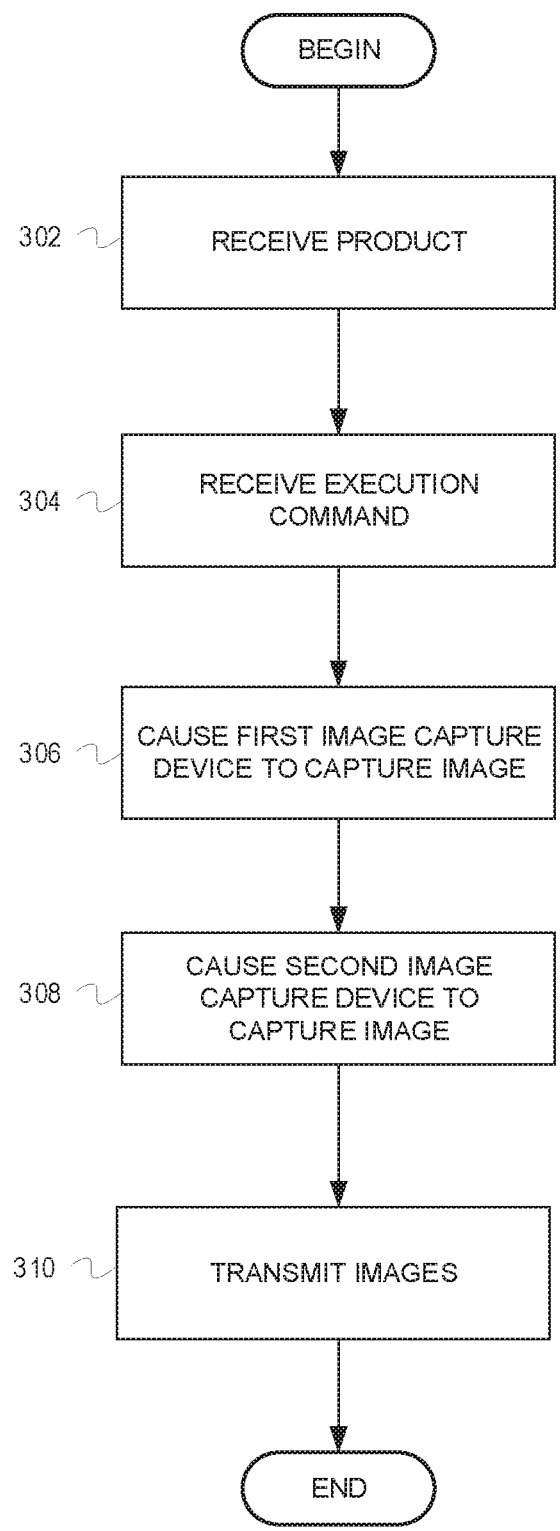
FIG. 3 is a flow chart depicting example operations for assessing a product, according to some embodiments.

While the discussion of FIG. 2 provides a discussion of a system for assessing products, the discussion of FIG. 3 describes example operations for assessing products.

FIG. 3 is a flow chart depicting example operations for assessing a product, according to some embodiments. The flow begins at block 302.

At block 302, a product is received. For example, the product can be received at a housing of an enclosure via a door. The enclosure includes a product holding surface, a lighting element, and an image capture device. The image capture device is configured to capture an image of the product. In the embodiment depicted in FIG. 3, the enclosure includes two image capture devices. Each of the image capture devices is configured to capture an image of the product from a different perspective (e.g., above, below, next to, etc. the product). In some embodiments, the image of the product is captured so that the product can be assessed. For example, the product can be assessed to determine its suitability for sale, as a sample to determine the suitability of a number of products, etc. The flow continues at block 304.

At block 304, an execution command is received. For example, the execution command can be received at a controller device that is separate from, or integrated with, the enclosure. The execution command instructs the enclosure to capture the image of the product. The execution command can be received from a user (e.g., user input device) or triggered automatically by the controller device (e.g., by placement of a product within the enclosure). In the latter, the controller device can "receive" the execution from itself in an automated fashion. The flow continues at block 306.

At block 306, a first image capture device is caused to capture a first image of a product. For example, the controller device can transmit a command to the first image capture device to capture the first image of the product. The first image of the product is captured from a first perspective. For example, the first image capture device may be above, next to, in front of, etc. the product. The flow continues at block 308.

At block 308, a second image capture device is caused to capture a second image of the product. For example, the controller device can transmit a command to the second image capture device to capture the second image of the product. The second image of the product is captured from a second perspective. For example, the second image capture device may be above, next to, in front of, etc. the product. In one embodiment, the enclosure includes a transparent or translucent product holding surface and the second image capture device is located below the product holding surface. In such embodiments, the image of the product from the second perspective is captured through the product holding surface. The flow continues at block 310.

At block 310, images are transmitted. For example, the controller device can transmit the images to a remote processing system. The remote processing system can use the images of the product to assess the product, as described in U.S. Provisional Application No. 62/509,945 for an automated inspection system.

In some embodiments, an enclosure for use in assessing products comprises a housing, wherein the housing includes a door configured to allow placement of a product within the housing, a product holding surface, wherein the product holding surface is located within the housing, wherein the product holding surface allows pictures to be taken through the product holding surface, wherein the product holding surface divides the housing into a first portion and a second portion, and wherein the product holding surface is configured to support the product, a first image capture device, wherein the first image capture device is located within the first portion of the housing, and wherein the first image capture device is configured to capture an image of the product from a first perspective, a second image capture device, wherein the second image capture device is located within the second portion of the housing, wherein the second image capture device is configured to capture an image of the product from a second perspective, and wherein the image of the product from the second perspective is captured through the product holding surface, and a lighting element, wherein the lighting element is located within the housing, and wherein the lighting element is configured to provide lighting within the housing.

In some embodiments, a system for assessing products comprises an enclosure, wherein the enclosure includes a housing, wherein the housing includes a door configured to allow placement of a product within the housing, a product holding surface, wherein the product holding surface is located within the housing, and wherein the product holding surface is configured to support the product, a first image capture device, wherein the first image capture device is located within the housing, and wherein the first image capture device is configured to capture an image of the product from a first perspective, and a lighting element, wherein the lighting element is located within the housing, and wherein the lighting element is configured to provide lighting with the housing, a controller device, wherein the controller device is communicatively coupled to the first image capture device and the lighting element, and wherein the controller device includes a user input device, wherein the user input device is configured to receive an execution command, and a control circuit, wherein the control circuit is configured to receive, from the user input device, the execution command, in response to receipt of the execution command, control the first image capture device and the lighting element, and transmit, to a remote processing system, an image of the product captured by the first image capture device, the remote processing system, wherein the remote processing system is communicatively coupled to the controller device, and wherein the remote processing system is configured to receive, from the controller device, the image of the product captured by the first image capture device, and perform, based on the image of the product captured by the first image capture device, an analysis on the product.

In some embodiments, an apparatus, and a corresponding method performed by the apparatus, comprises receiving, in an enclosure, a product, wherein the enclosure includes a product holding surface that creates a first portion of the enclosure and a second portion of the enclosure, a first image capture device located in the first portion of the enclosure and second image capture device located in a second portion of the enclosure, wherein the first image capture device is configured to capture an image of the product from a first perspective, wherein the second image capture device is configured to capture an image of the product from a second perspective, and wherein the image of the product from the second perspective is captured through the product holding surface, receiving, via a controller device, an execution command, causing, by the controller device, the first image capture device to capture the image of the product from the first perspective, causing, by the controller device, the second image capture device to capture the image of the product from the second perspective, and transmitting, by the controller device to a remote processing system for analysis, the image of the product from the first perspective and the image of the product from the second perspective.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. An enclosure for use in assessing products, the enclosure comprising:
    a housing, wherein the housing includes a door configured to allow placement of a product within the housing;
    a product holding surface, wherein the product holding surface is located within the housing, wherein the product holding surface allows pictures to be taken through the product holding surface, wherein the product holding surface divides the housing into a first portion and a second portion, and wherein the product holding surface is configured to support the product;
    a first image capture device, wherein the first image capture device is located within the first portion of the housing and overlays a portion of the product holding surface, and wherein the first image capture device is directed toward a first location on the product holding surface and configured to capture an image of the product from a first, top view, perspective;
    a second image capture device, wherein the second image capture device is located within the second portion of the housing and underlays a portion of the product holding surface, wherein the second image capture device is directed toward the first location on the product holding surface and configured to capture an image of the product from a second, bottom view, perspective, wherein the first location for the first image capture device and the first location for the second image capture device are a same location, and wherein the image of the product from the second perspective is captured through the product holding surface; and
    a lighting element, wherein the lighting element is located within the housing, and wherein the lighting element is configured to provide lighting within the housing.

2. The enclosure of claim 1, wherein the enclosure further comprises:
    a controller device, wherein the controller device is communicatively coupled to the first image capture device, the second image capture device, and the lighting element, and wherein the controller device is configured to control action of the first image capture device, the second image capture device, and the lighting element.

3. The enclosure of claim 1, wherein the product holding surface is substantially transparent.

4. The enclosure of claim 1, wherein the product holding surface is made of one or more of plastic and glass.

5. The enclosure of claim 1, wherein the product holding surface includes a product barrier.

6. The enclosure of claim 5, wherein the product barrier comprises one or more of an incline, a ledge, a ridge, and a wall.

7. The enclosure of claim 1, wherein the first portion of the housing is above the product holding surface and the second portion of the housing is below the product holding surface.

8. A system for assessing products, the system comprising:
    an enclosure, wherein the enclosure includes:
        a housing, wherein the housing includes a door configured to allow placement of a product within the housing;
        a product holding surface, wherein the product holding surface is located within the housing, and wherein the product holding surface is configured to support the product;
        a first image capture device, wherein the first image capture device is located on a first side of the product holding surface and overlays a portion of the product holding surface, and wherein the first image capture device is directed toward a first location on the product holding surface configured to capture an image of the product from a first, top view, perspective;
        a second image capture device, wherein the second image capture device is located on a second side of the product holding surface and underlays a portion of the product holding surface, and wherein the second image capture device is directed toward the first location on the product holding surface and configured to capture an image of the product from a second, bottom view, perspective, wherein the first location for the first image capture device and the first location for the second image capture device are a same location, and wherein the image of the product from the second perspective is captured through the product holding surface; and
        a lighting element, wherein the lighting element is located within the housing, and wherein the lighting element is configured to provide lighting with the housing;
    a controller device, wherein the controller device is communicatively coupled to the first image capture device and the lighting element, and wherein the controller device includes:
        a user input device, wherein the user input device is configured to receive an execution command; and
        a control circuit, wherein the control circuit is configured to:
            receive, from the user input device, the execution command;
            in response to receipt of the execution command, control the first image capture device and the lighting element; and
            transmit, to a remote processing system, an image of the product captured by the first image capture device;
    the remote processing system, wherein the remote processing system is communicatively coupled to the controller device, and wherein the remote processing system is configured to:
        receive, from the controller device, the image of the product captured by the first image capture device; and perform, based on the image of the product captured by the first image capture device, an analysis on the product.

9. The system of claim 8, wherein the product holding surface is substantially transparent.

10. The system of claim 9, wherein the product holding surface is made of one or more of plastic and glass.

11. The system of claim 8, wherein the product holding surface includes a product barrier.

12. The system of claim 11, wherein the product barrier comprises one or more of an incline, a ledge, a ridge, and a wall.

13. A method for assessing products, the method comprising:

receiving, in an enclosure, a product, wherein the enclosure includes a product holding surface that creates a first portion of the enclosure and a second portion of the enclosure, a first image capture device located in the first portion of the enclosure and overlaying a portion of the product holding surface, and a second image capture device located in a second portion of the enclosure and underlaying a portion of the product holding surface, wherein the first image capture device is directed toward a first location on the product holding surface and configured to capture an image of the product from a first, top view, perspective, wherein the second image capture device is directed toward the first location on the product holding surface and configured to capture an image of the product from a second, bottom view, perspective, wherein the first location for the first image capture device and the first location for the second image capture device are a same location, and wherein the image of the product from the second perspective is captured through the product holding surface;

receiving, via a controller device, an execution command;

causing, by the controller device, the first image capture device to capture the image of the product from the first perspective;

causing, by the controller device, the second image capture device to capture the image of the product from the second perspective; and transmitting, by the controller device to a remote processing system for analysis, the image of the product from the first perspective and the image of the product from the second perspective.

14. The method of claim 13, wherein the product holding surface is substantially transparent.

15. The method of claim 13, wherein the product holding surface is made of one or more of plastic and glass.

16. The method of claim 13, wherein the product holding surface includes a product barrier.

17. The method of claim 16, wherein the product barrier comprises one or more of an incline, a ledge, a ridge, and a wall.

18. The method of claim 13, wherein the first portion of the housing is above the product holding surface and the second portion of the housing is below the product holding surface.

19. The method of claim 13, wherein the product holding surface is moveable within the enclosure.

20. The enclosure of claim 1, wherein the product is a single product, wherein the image of the product from the first perspective is a first image of the single product, and wherein the image of the product from a second perspective is a second image of the single product.

* * * * *